(12) United States Patent
Ji et al.

(10) Patent No.: US 6,638,722 B2
(45) Date of Patent: Oct. 28, 2003

(54) METHOD FOR RAPID AMPLIFICATION OF DNA

(75) Inventors: Wan Ji, Austin, TX (US); Keqin Gregg, Austin, TX (US); Bonnie Reus, Cedar Park, TX (US); Jon Kemppainen, Austin, TX (US); Kristen Taylor, Austin, TX (US); Scott Davis, Bertram, TX (US)

(73) Assignee: Invitrogen Corporation, Carlsbad, CA (US)

( * ) Notice: Subject to any disclaimer, the term of this patent is extended or adjusted under 35 U.S.C. 154(b) by 0 days.

(21) Appl. No.: 09/881,565

(22) Filed: Jun. 13, 2001

(65) Prior Publication Data

US 2003/0108870 A1 Jun. 12, 2003

(51) Int. Cl.$^7$ .............................. C12Q 1/68; C12P 19/34
(52) U.S. Cl. ........................................... 435/6; 435/91.2
(58) Field of Search .................................... 435/6, 91.2

(56) References Cited

U.S. PATENT DOCUMENTS

| | | | | |
|---|---|---|---|---|
| 5,104,792 A | * | 4/1992 | Silver et al. .................... | 435/6 |
| 5,496,562 A | | 3/1996 | Burgoyne ................... | 424/488 |
| 5,731,171 A | | 3/1998 | Bohlander .................. | 435/91.2 |
| 5,945,283 A | * | 8/1999 | Kwok et al. ..................... | 435/6 |
| 6,066,457 A | * | 5/2000 | Hampson et al. ............... | 435/6 |
| 6,379,932 B1 | * | 4/2002 | Arnold et al. ........... | 435/91.51 |

OTHER PUBLICATIONS

Albani, et al., "PCR amplification of microdissected wheat chromosome arms in a simple 'single tube' reaction," The Plant Journal, 4:899–903, 1993.
Cheung, et al., "Whole genome amplification using a degenerate oligonucleotide primer allows hundreds of genotypes to be performed on less than one nanogram of genomic DNA," Proc. Nat. Acad. Sci. USA, 93:14676–79, 1996.
Grothues, et al., "PCR amplification of megabase DNA with tagged random primers (T–PCR)," Nucleic Acids Res., 21:1321–22, 1993.
Kinzler, et al., "Whole genome PCR: application to the identification of sequences bound by gene regulatory proteins," Nucleic Acids Res., 17:3645–53, 1989.
Peng, et al., "Multiple PCR analyses on trace amounts of DNA extracted from fresh and paraffin wax embedded tissues after random hexamer primer PCR amplification," J. Clin. Pathol., 47:605–08, 1994.
Sutcliffe, et al., "PCR Amplification and Analysis of Yeast Artificial Chromosomes," Genomics,. 13:1303–06, 1992.
Telenius, et al., "Degenerate Oligonucleotide–Primed PCR: General Amplication of Target DNA by a Single Degenerate Primer," Genomics, 13:718–25, 1992.
Wells, et al., "Detailed chromosomal and molecular genetic analysis of single cells by whole genome amplification and comparative genomic hybridization," Nucelic Acids Res., 27:1214–18, 1998.
Wong, et al., "Use of tagged random hexamer amplification (TRHA) to clone and sequence minute quantities of DNA–application to a 180 kb plasmid isolated from Spingomonas F199," Nucleic Acids Res., 24:3778–83, 1996.
Zhang, et al., "Whole genome amplification from a single cell: Implications for genetic analysis," Proc. Natl. Acad. Sci. USA, 89:5847–58, 1992.
Zheleznaya, et al., "PCR Fragmentation of DNA," Biochemistry (Moscow), 64:373–78, 1999.
Zhou, et al., "Comparison of Two PCR Techniques Used in Amplification of Microdissected Plant Chromosomes from Rice and Wheat," BioTechniques, 28:766–74, 2000.

\* cited by examiner

Primary Examiner—Kenneth R. Horlick
(74) Attorney, Agent, or Firm—Vinson & Elkins L.L.P.

(57) ABSTRACT

The present disclosure relates to methods of DNA amplification with a first primer that has a random sequence of nucleotides at its 3' end and a generic sequence 5' of the random nucleotides, as well as a second primer with the generic sequence of the first primer. The disclosure further relates to a method of precipitating DNA on a solid medium to improve DNA amplification. In a preferred embodiment, the presently disclosed methods are used for high-throughput genotyping of DNA samples, such as bloodstains or trace amounts of DNA.

34 Claims, 6 Drawing Sheets

US 6,638,722 B2

METHOD FOR RAPID AMPLIFICATION OF DNA

STATEMENT REGARDING FEDERALLY SPONSORED RESEARCH OR DEVELOPMENT

Not applicable.

REFERENCE TO A "MICROFICHE APPENDIX"

Not applicable.

BACKGROUND OF THE INVENTION

1. Field of the Invention

The present disclosure relates generally to the field of DNA amplification and more particularly to the field of amplifying any stretch of DNA in a sequence-independent manner.

2. Description of Related Art

The following description includes information that may be useful in understanding the present disclosure. It is not an admission that any of the information provided herein is prior art, or relevant, to the presently claimed inventions, or that any publication specifically or implicitly referenced is prior art.

It is well known that there is often an association between genetic variation and phenotype manifestation. Genetic variations and their associated phenotypes are studied using various methods of genotyping genomic DNA. A Single Nucleotide Polymorphism (SNP) is a single nucleotide variation at a specific location in the genome of different individuals. SNPs are stable genetic variations frequently found in genes, and contribute to the wide range of phenotypic variations found in organisms. SNP genotyping is useful in developing detailed genetic and physical maps of chromosomes. Genotyping densely distributed SNP markers across the different chromosomes of an individual can help reveal statistically significant correlations between chromosomal loci and phenotypic expression. Extensive genotyping, however, requires not only a simple and rapid way for obtaining, shipping, storing, and sorting large amounts of genetic material, but also convenient and high-throughput methods for extracting large quantities of DNA from these samples.

There are a variety of available methods for obtaining and storing tissue and/or blood samples. These alternatives allow tissue and blood samples to be stored and transported in a form suitable for the recovery of genomic DNA from the samples for genotype analysis. DNA samples can be collected and stored on a variety of solid mediums, including Whatmann® paper, Guthrie cards, tubes, swabs, filter paper, slides, or other containers. When whole blood is collected on filter paper, for example, it can be dried and stored at room temperature.

One known and more frequently used method for securing and storing DNA is described in U.S. Pat. No. 5,496,562. This method involves storing dried animal blood samples on chemically treated filter paper, called FTA paper, that protects genomic DNA from degrading (commercially available as FTA™ paper by Whatman®). FTA paper is light weight and easy to store, which makes it a popular choice for collecting genetic material and samples. Samples on FTA paper are conveniently stored and shipped at room temperature.

All of the materials available to those of skill in the art for storing blood or other tissues containing DNA have limitations. For example, the amount of tissue or blood collected may be very limited, which makes wide-scale and high-throughput genotyping impractical and expensive. For example, despite the widespread use of FTA paper, its usefulness is limited because the stored bloodstains contain only a small amount of genomic DNA. A 6.0 $cm^2$ piece of FTA paper only preserves approximately 100 $\mu$l of blood, equivalent to approximately 1.0 $\mu$g of DNA. While it is possible to extract genomic DNA from a larger piece of FTA paper, the size of the paper makes it cumbersome to manipulate in the small wells of a 96-well plate or a 384-well plate, both of which are important tools for high-throughput screening of large numbers of DNA samples. Therefore, the usefulness of a tool like FTA paper has been restricted to low-volume genotyping.

The limited amount of DNA stored on FTA paper also makes it impractical for genotyping multiple polymorphisms and genetic loci in a single organism. The FTA paper sample can be cut into smaller pieces for genotyping multiple SNPs; a small circle of 1.0–2.0 $mm^2$ diameter of the sample contains about 1–5 ng of genomic DNA, which is sufficient for one polymerase chain reaction (PCR). But this approach is undesirable because it requires repetitive cutting, sorting, and extracting of the FTA paper, which is not only tedious but also prone to human error. For a genomic scan of hundreds or thousands of SNPs, the task of cutting and analyzing DNA samples stored on FTA paper is an insurmountable barrier for researchers.

Additionally, the strong adherence between DNA and FTA paper makes DNA extraction for analysis difficult. Although proteinase K and endonuclease digestion can facilitate DNA release as suggested by the manufacturer, this approach is too complicated and expensive for high-throughput operations. The commercially available FTA Purification Reagent, which can be used to prepare DNA stored on FTA paper for analysis by PCR™ yields inconsistent results. For example, often no specific DNA amplification is achieved after the DNA sample is processed using this reagent, which is unacceptable in a high-throughput operation. The manufacturer also suggests that the strong adhesion of DNA to FTA paper allows for repeated genotyping of DNA stored on FTA paper. Notwithstanding the fact that PCR efficacy for "recycled" FTA paper has not been fully tested, cleaning the tiny FTA papers between consecutive SNP PCRs is impractical for high-throughput processing. The small pieces of floating filter paper are difficult to wash by conventional aspiration, and they tend to clog aspiration needles or pipette tips. Further, small pieces are easily lost during the cleaning process. Finally, repeated pipetting of PCR products has an associated risk of cross contamination among different wells.

The shortcomings associated with small samples of blood or tissue from an organism are overcome by efficient methods of whole genomic DNA amplification. For example, whole genomic DNA amplified from the small amounts of DNA sample stored on FTA paper could be used in multiple PCR reactions to extensively genotype various polymorphisms such as SNPs found in a single organism in a high-throughput screening process. Nevertheless, while several methods for whole genome amplification have been proposed and successfully used for various applications in the past, these methods are generally inefficient, complex, and expensive. Therefore, the need exists for a simple and cost effective way of amplifying genomic DNA from small samples of blood or tissue.

One of the first methods for amplifying DNA was the linker adaptor-mediated PCR (LAM-PCR) approach, which has been applied to microdissected chromosomes (Zhou et al., *Bio Techniques* 28:766–774, 2000; Albani et al., *Plant J* 4(5):899–903, November 1993), yeast artificial chromosome (YAC) DNA (Sutcliffe et al., *Genomics* 13(4):1303–6, 1992), and genomic DNA (Kinzler et al., *Nucleic Acids Res* 25:17(10):3645–53, May 1989). In this approach, the starting DNA is first digested with a restriction enzyme, usually an enzyme with a four base recognition sequence. After inactivation of the restriction enzyme, a known sequence (either an adaptor or a synthetic linker) is ligated to the ends of the DNA fragments generated by the restriction-enzyme digest, providing primer binding sites for PCR amplification. The DNA can then be amplified by PCR using primers that are complementary to the sequence of the adaptor or linker.

Unfortunately, the usefulness of LAM-PCR is limited because it involves multiple steps, including DNA fragmentation, adaptor or linker ligation, and PCR amplification. These steps make this process both laborious and expensive for high-throughput genotyping. An additional shortcoming of this method is that sequences that do not contain the recognition sequence of the restriction enzyme used at appropriately spaced intervals will not be amplified by PCR because the regions will be too long to amplify. This method is also time-consuming and cumbersome because of the extensive manipulations of DNA necessary to attach the known sequences to both ends of the fragments, especially when applied to small quantities of DNA, such as microdissected chromosomal pieces, or DNA found in bloodstains or small samples of tissue.

Another more restrictive method available for amplifying genomic DNA uses inter-ALU PCR (more generally known as inter-repetitive element PCR), which relies on the presence of appropriately spaced and oriented ALU repetitive elements or other repeated sequences. Inconsistent results are obtained, however, with low complexity DNA sources such as YACs, cosmids, or phage, because of the low incidence of these repeat sequences. Other inconsistencies arise because repeated sequences do not occur uniformly throughout the genome, and thus a sequence of interest occurring in an area in which the necessary repeated sequences are rare or absent will not be amplified. Another major limitation of this method is that it is species specific. For example, the use of this method is restricted to DNA of the species from which the repetitive elements are derived and for which the PCR primers were constructed.

A method called degenerated oligonucleotide-primed PCR (DOP-PCR) utilizes partially degenerated sequence (6 out of 21) and repeated thermocycling Telenius, et al., *Genomics* 13(3):718–25, 1992. In the DOP-PCR method, the first rounds of PCR amplification have a low primer annealing temperature of around 30° C. The primer used consists of a random hexamer that is flanked on the 3' side by a defined hexamer and on the 5' side by a defined sequence. Because the 3' end of the primer has a defined hexamer, the target sequence must match this hexamer in order to amplify. Therefore, the number of sequences that will be amplified by this method are limited. The inadequacy of the DOP-PCR method is further demonstrated when it is applied to DNA sources of limited complexity such as YACs, cosmids, or phage inserts. The resulting product is not a smear on a ethidium bromide stained agarose gel (as occurs with randomly amplified DNA), but rather distinct bands, indicating that hybridization occurs at relatively few sites and thus sequence independent amplification is not achieved.

Another attempt to amplify genomic DNA was a method termed primer-extension preamplification (PEP) (Zhang et al., *Proc. Natl. Acad. Sci. USA* 89:5847–5851, 1992). The PEP method utilizes 15 base pair (bp) random oligonucleotides and repeated thermocycling to randomly prime multiple sites in the genomic DNA for PCR. A method utilizing 6 base pair (bp) random oligonucleotides and PCR has also been reported (Peng et al., *Clin Pathol* 47:605–608,1994). Although both PEP and DOP-PCR have been employed in several specific applications, they are consistently hampered by their relatively low amplification efficiency (Wells et al., *Nucleic Acids Res* 27:1214–1218, 1999). A possible explanation for this low efficiency is that because the primers contain random nucleotides and therefore form a large spectrum of different oligonucleotides, the effective concentration of any specific primer is very low, which may limit the exponential amplification of PCR. Additionally, the non-specific binding of the random oligonucleotides tends to initiate DNA synthesis within the PCR products of previous rounds. Therefore, the size of the PCR products decreases constantly with each additional round of PCR amplification, which renders the final PCR products very small, especially when a large number of PCR cycles are performed. These small PCR products are not as useful as larger pieces of amplified DNA for the subsequent genetic analysis of the DNA or genotype analysis.

Another method of genomic DNA amplification, termed tagged random PCR, was described by Grothues et al. (*Nucleic Acids Res* 21:1321–1322, 1993) and Wong et al. (*Nucleic Acids Res* 24:3778–83,1996). This method attempts to overcome the shortcomings associated with PEP and DOP-PCR by separating random priming and PCR amplification into two steps and amplifying whole genomic DNA with a single PCR primer. In the first amplification step, tagged random primers consisting of a random 6 bp or 9 to 15 bp 3' tail and a constant 17 to 22 bp 5' head indiscriminately prime the genomic DNA. Next, unincorporated tagged primers are removed by gel filtration using a Biogel P100 spin column or a Centricon-100 spin column. In the second amplification step, the DNA molecules fitted with the 5' constant head and its reverse complement at both ends are amplified by PCR. Although the scheme can amplify whole genomic DNA, its multiple steps of reaction and purification are too complex and expensive for high-throughput screening.

The construction of libraries from microdissected chromosomal bands is an elegant way to obtain DNA probes from genomic regions of particular interest. The applicability of this approach has been restricted by the time consuming and technically difficult process of amplifying DNA from microdissected material. Traditionally, DNA from 20 to 30 microdissected chromosomal bands is collected in a small droplet. The DNA is then subjected to various manipulations before it is used for PCR amplification. These manipulations include phenol/chloroform extractions, restriction enzyme digestion and ligation to a vector or linker (LAM-PCR). These steps must be performed in very small volumes on the stage of a microscope with specialized equipment (Kao et al., *Proc Natl Acad Sci USA* 1:88(5):1984–8,1991), which severely limits the usefulness of this technique.

Yeast artificial chromosomes (YACs) are ideal vectors for the detailed mapping of large stretches of DNA. One of the main disadvantages of the YAC cloning system is that there have been no methods available to purify YAC DNA in large quantities. High molecular weight DNA can be prepared from yeast clones carrying YACs and the YACs can be isolated on a pulsed field gel. This approach, however, yields only very small amounts of pure YAC DNA. This is a major disadvantage because many important uses of these large inserts, e.g. screening of cDNA libraries or Fluorescent in situ hybridization (FISH) analysis, require larger amounts of purified YAC DNA.

Thus, a need exists for a more efficient and inexpensive method for amplifying DNA samples that is compatible with high-throughput screening, is sequence independent, applicable to any type of DNA, useful for amplifying DNA from any species, and most important, capable of amplifying extremely limited amounts of DNA. There is also a need for an amplification process that is simple (to avoid the problem of PCR contamination), has high fidelity in reproducing genetic material, and has a low rate of distortion of amplified sequences.

BRIEF SUMMARY OF THE INVENTION

The present disclosure seeks to overcome the drawbacks inherent in other methods of DNA amplification by providing a simple and direct method for amplifying DNA. The method of the present disclosure preferably amplifies DNA in a sequence-independent manner using a single reaction mixture and a single programmable thermocycling reaction. This method can be used to amplify trace amounts of DNA, including genomic DNA from small tissue or blood samples, such as fine needle aspirates or single tissue sections, or even from a single cell. The single reaction mixture used in this method also greatly reduces the risk of sample contamination and facilitates high-throughput screening, and in a preferred embodiment a single heat-stable DNA polymerase is included to amplify all DNA in the single reaction mixture. This method allows DNA to be amplified from any species or organism. It is understood that the present disclosure encompasses sequence independent amplification of DNA from any source, including but not limited to human, animal, plant, yeast, viral, eukaryotic, and prokaryotic DNA.

The present disclosure also offers an improved method for processing DNA samples on a solid medium. Other known methods of preparing DNA samples stored on a solid medium for genetic analysis or DNA amplification are inefficient and inconsistent, thereby limiting the usefulness of the information obtained from the DNA samples. The method of the present disclosure seeks to overcome the drawbacks inherent in these other methods by greatly simplifying the preparation of DNA samples and improving the DNA for subsequent analysis. The method of the present disclosure precipitates the DNA sample on a solid medium using methods well known to those of skill in the art. In a preferred embodiment, the DNA sample is a bloodstain on a solid medium. The DNA processed according to the presently disclosed method can be subsequently subjected to DNA amplification using the presently disclosed methods and/or genetic analysis. This disclosed precipitation method produces more consistent results, reduces the cost of high-throughput operations, and improves the quality of DNA amplified from the DNA sample.

The present disclosure includes methods of amplifying DNA from a DNA sample. In a preferred embodiment, the method of amplifying DNA uses a reaction mixture that contains a DNA sample; a first primer with a random sequence of nucleotides at its 3' end and a generic sequence 5' of the random nucleotides; and a second primer that has the generic sequence of the first primer but lacks the random sequence of the first primer. In a preferred embodiment, a single reaction mixture is used. An example of a first primer is the sequence designated SEQ ID NO:1, and an example of the second primer is the sequence designated SEQ ID NO:2. Preferably, the reaction mixture contains other components that are necessary for DNA amplification, which are well known to those of skill in the art.

The DNA sample in the reaction mixture is subjected to DNA amplification by a first DNA polymerase, wherein the first primer anneals to the DNA to allow the first DNA polymerase to synthesize a complementary DNA strand from the 3' end of the first primer to produce a DNA product. The steps for DNA amplification by the first DNA polymerase are denaturing the DNA product; annealing the first primer with the DNA to allow the formation of a DNA-primer hybrid; and incubating the DNA-primer hybrid to allow the first DNA polymerase to extend the primer and synthesize the DNA product. Preferably, these DNA amplification steps are repeated at least one time. In a preferred embodiment, the annealing temperature and the incubating temperature are the same. In another preferred embodiment, the DNA product produced by the DNA amplification is flanked by the generic sequence and reverse complement of the generic sequence.

This DNA product is then subjected to DNA amplification by a heat-stable DNA polymerase, wherein the second primer anneals to the DNA product and the heat-stable DNA polymerase synthesizes a complementary DNA strand from the 3' end of the second primer to produce a second DNA product. The steps for DNA amplification by the heat-stable DNA polymerase are denaturing the DNA product; annealing the second primer with the DNA product to allow the formation of a DNA-primer hybrid; and incubating the DNA-primer hybrid to allow the heat-stable DNA polymerase to synthesize the second DNA product. Preferably, these DNA amplification steps are repeated about 30 to about 35 times, and more preferably about 40 times. In a preferred embodiment, the second DNA product is flanked by the generic sequence and the reverse complement of the generic sequence. In another preferred embodiment, the annealing temperature is higher than the optimal annealing temperature of the random sequence of nucleotides at the 3' end of the first primer.

In a preferred embodiment, the first DNA polymerase has 5' to 3' exonuclease activity or primer displacement activity. The first DNA polymerase is preferably E.coli DNA polymerase I, and the heat-stable DNA polymerase is preferably Taq DNA polymerase. In another preferred embodiment, the first DNA polymerase and the heat-stable DNA polymerase are the same DNA polymerase, and that DNA polymerase is Taq DNA polymerase.

In another preferred embodiment, the first primer has about 4 to about 8 random nucleotides at its 3' end. In a more preferred embodiment, the first primer has about 6 random nucleotides at its 3' end. Preferably the generic sequence of the first primer is about 15 to about 28 nucleotides in length, or more preferably about 20 to about 25 nucleotides in length. The random nucleotides of the first primer may also be G:C rich or A:T rich, to preferably amplify certain regions of the DNA sample. Finally, the generic sequence of the first primer preferably will have a single or multiple restriction enzyme recognition site, which will facilitate subcloning of the amplified DNA products.

In a preferred embodiment, the DNA sample is genomic DNA, microdissected chromosome DNA, yeast artificial chromosome (YAC) DNA, cosmid DNA, phage DNA, P1 derived artificial chromosome (PAC) DNA, or bacterial artificial chromosome (BAC) DNA. In another preferred embodiment, the DNA sample is mammalian DNA, plant DNA, yeast DNA, viral DNA, or prokaryotic DNA. In yet another preferred embodiment, the DNA sample is obtained from a human, bovine, porcine, ovine, equine, rodent, avian, fish, shrimp, plant, yeast, virus, or bacteria. Preferably the DNA sample is genomic DNA, wherein the method of amplifying DNA includes DNA amplification with a fluorescent label. In another preferred embodiment, the DNA sample is bovine DNA. Preferably, the DNA sample is tissue on a solid medium, wherein the tissue is blood, preferably in the form of a bloodstain. In a preferred embodiment, the solid medium is filter paper, wherein the filter paper is chemically treated, for example FTA™ paper. In a preferred embodiment the bloodstain is from a mammal, and the mammal is preferably human, bovine, or porcine. The DNA sample may be obtained from many sources well known to those of skill in the art, including but not limited to a buccal swab, a nose swab, blood, cord blood, amniotic fluid, embryonic tissue, hair, endothelial cells, hoof clippings, or fingernail clipping.

In another preferred embodiment, the method of amplifying DNA further includes genotype analysis of the amplified DNA product. Alternatively, the method of amplifying DNA preferably further includes identifying a single nucleotide polymorphism (SNP) in the amplified DNA product. In preferred embodiments, a SNP may be identified in the DNA of an organism by a number of methods well known to those of skill in the art, including but not limited to identifying the SNP by DNA sequencing, by amplifying a PCR product and sequencing the PCR product, by Oligonucleotide Ligation Assay (OLA), by Doublecode OLA, by Single Base Extension Assay, by allele specific primer extension, or by mismatch hybridization. Preferably the identified SNP is associated with a phenotype, including disease phenotypes and desirable phenotypic traits. The amplified DNA generated by using the disclosed method of DNA amplification may also preferably be used to generate a DNA library, including but not limited to genomic DNA libraries, microdissected chromosome DNA libraries, BAC libraries, YAC libraries, PAC libraries, cDNA libraries, phage libraries, and cosmid libraries.

Another aspect of the present disclosure is a preferred method of amplifying DNA that uses a reaction mixture with a DNA sample; a first primer with a random sequence of nucleotides at its 3' end and a generic sequence 5' of the random nucleotides; a second primer with the generic sequence of the first primer and lacking the random sequence of the first primer; and a heat-stable DNA polymerase. In a preferred embodiment, a single reaction mixture is used. Preferably, the reaction mixture also contains other components that are necessary for DNA amplification, which are well known to those of skill in the art. In a preferred embodiment, the heat-stable DNA polymerase is Taq DNA polymerase, the DNA sample is a bloodstain on a solid medium, and the DNA sample is preferably dehydrated on the solid medium.

The DNA sample in the reaction mixture is subjected to DNA amplification wherein the first primer anneals to the DNA to allow the heat-stable DNA polymerase to synthesize a complementary DNA strand from the 3' end of the first primer to produce a DNA product. The steps for DNA amplification by the heat-stable DNA polymerase are denaturing the DNA product; annealing the first primer with the DNA to allow the formation of a DNA-primer hybrid; and incubating the DNA-primer hybrid to allow the heat-stable DNA polymerase to synthesize the DNA product. Preferably, these DNA amplification steps are repeated at least one time. In a preferred embodiment, the annealing temperature and the incubating temperature are the same. In another preferred embodiment, the DNA product produced by the DNA amplification is flanked by the generic sequence and reverse complement of the generic sequence.

This DNA product is then subjected to DNA amplification by the heat-stable DNA polymerase, wherein the second primer anneals to the DNA product and the heat-stable DNA polymerase synthesizes a complementary DNA strand from the 3' end of the second primer to produce a second DNA product. The steps for DNA amplification by the heat-stable DNA polymerase are denaturing the DNA product; annealing the second primer with the DNA product to allow the formation of a DNA-primer hybrid; and incubating the DNA-primer hybrid to allow the heat-stable DNA polymerase to synthesize the second DNA product. Preferably, these DNA amplification steps are repeated about 30 to about 35 times, and more preferably about 40 times. In a preferred embodiment, the second DNA product is flanked by the generic sequence and reverse complement of the generic sequence. In another preferred embodiment, the annealing temperature is higher than the optimal annealing temperature of the random sequence of the first primer.

In another preferred method of amplifying DNA, a reaction mixture is provided that has a DNA sample, wherein the DNA sample is a tissue on a solid medium; a first primer with a random sequence of nucleotides at its 3' end and a generic sequence 5' of the random nucleotides; a second primer with the generic sequence of the first primer and lacking the random sequence of the first primer; and a heat-stable DNA polymerase. In a preferred embodiment, a single reaction mixture is used. In a preferred embodiment, the tissue on the solid medium is blood. In another preferred embodiment the solid medium is filter paper, and the filter paper is chemically treated. The DNA sample is preferably dehydrated on the filter paper. Preferably, the reaction mixture also contains other components that are necessary for DNA amplification, which are well known to those of skill in the art. In a preferred embodiment, the heat-stable DNA polymerase is Taq DNA polymerase, the DNA sample is a bloodstain on a solid medium, and the DNA sample is preferably dehydrated on the solid medium.

The DNA sample in the reaction mixture is subjected to DNA amplification by a heat-stable DNA polymerase, wherein the first primer anneals to the DNA to allow the heat-stable DNA polymerase to synthesize a complementary DNA strand from the 3' end of the first primer to produce a DNA product. The steps for DNA amplification by the heat-stable DNA polymerase are denaturing the DNA product; annealing the first primer with the DNA to allow the formation of a DNA-primer hybrid; and incubating the DNA-primer hybrid to allow the heat-stable DNA polymerase to synthesize the DNA product. Preferably, these DNA amplification steps are repeated at least one time. In a preferred embodiment, the annealing temperature and the incubating temperature are the same. In another preferred embodiment, the DNA product produced by the DNA amplification is flanked by the generic sequence and reverse complement of the generic sequence.

This DNA product is then subjected to DNA amplification by the heat-stable DNA polymerase, wherein the second primer anneals to the DNA product and the heat-stable DNA polymerase synthesizes a complementary DNA strand from the 3' end of the second primer to produce a second DNA product. The steps for DNA amplification by the heat-stable DNA polymerase are denaturing the DNA product; annealing the second primer with the DNA product to allow the formation of a DNA-primer hybrid; and incubating the DNA-primer hybrid to allow the heat-stable DNA polymerase to synthesize the second DNA product. Preferably, these DNA amplification steps are repeated about 30 to about 35 times, and more preferably about 40 times. In a preferred embodiment, the second DNA product is flanked by the generic sequence and reverse complement of the generic sequence. In another preferred embodiment, the annealing temperature is higher than the optimal annealing temperature of the random sequence of nucleotides at the 3' end of the first primer.

Another aspect of the present disclosure is a preferred method of identifying a polymorphism, which uses a reaction mixture with a DNA sample; a first primer with a random sequence of nucleotides at its 3' end and a generic sequence 5' of the random nucleotides; and a second primer with the generic sequence of the first primer and lacking the random sequence of the first primer. In a preferred embodiment, a single reaction mixture is used. Preferably, the reaction mixture also contains other components that are necessary for DNA amplification, which are well known to those of skill in the art. In a preferred embodiment, the amplified DNA products are analyzed to identify a polymorphism, and preferably the polymorphism is a single nucleotide polymorphism (SNP). The methods of identifying SNPs are well known to those of skill in the art. In a preferred embodiment of identifying a SNP, the SNP is identified by DNA sequencing, Oligonucleotide Ligation Assay (OLA), Doublecode OLA, Single Base Extension Assay, allele specific primer extension, or mismatch hybridization.

The DNA sample in the reaction mixture is subjected to DNA amplification by a first DNA polymerase, wherein the first primer anneals to the DNA to allow the first DNA polymerase to synthesize a complementary DNA strand from the 3' end of the first primer to produce a DNA product. The steps for DNA amplification by the first DNA polymerase are denaturing the DNA product; annealing the first primer with the DNA to allow the formation of a DNA-primer hybrid; and incubating the DNA-primer hybrid to allow the first DNA polymerase to synthesize the DNA product. Preferably, these DNA amplification steps are repeated at least one time. In a preferred embodiment, the DNA product produced by the DNA amplification is flanked by the generic sequence and reverse complement of the generic sequence.

This DNA product is then subjected to DNA amplification by a heat-stable DNA polymerase, wherein the second primer anneals to the DNA product to allow the heat-stable DNA polymerase to produce amplified DNA products. The amplified DNA products are produced when the heat-stable DNA polymerase synthesizes a complementary DNA strand from the 3' end of the second primer annealed to the DNA product. The steps for DNA amplification by the heat-stable DNA polymerase are denaturing the DNA product; annealing the second primer with the DNA product to allow the formation of a DNA-primer hybrid; and incubating the DNA-primer hybrid to allow the heat-stable DNA polymerase to synthesize the amplified DNA products. The amplified DNA products are then preferably analyzed to identify a polymorphism. Preferably, these DNA amplification steps are repeated about 30 to about 35 times, and more preferably about 40 times. In a preferred embodiment, the amplified DNA products are flanked by the generic sequence and reverse complement of the generic sequence. In another preferred embodiment, the annealing temperature is higher than the optimal annealing temperature of the random sequence of nucleotides at the 3' end of the first primer.

Another aspect of the present disclosure is a preferred method of amplifying DNA that uses a reaction mixture with a DNA sample to be amplified; a first primer with a random sequence of nucleotides at its 3' end and a generic sequence 5' of the random nucleotides; and a second primer with the generic sequence of the first primer and lacking the random sequence of the first primer. Preferably, the reaction mixture also contains other components that are necessary for DNA amplification, which are well known to those of skill in the art. In a preferred embodiment, the DNA sample is tissue on a solid medium, and the DNA sample is preferably dehydrated on the solid medium.

The DNA sample in the reaction mixture is heated to a temperature that denatures the DNA to be amplified, cooled to a temperature that allows the random sequence of the first primer to hybridize to its complement DNA, and incubated to allow synthesis of a DNA product by a DNA polymerase. In a preferred embodiment the DNA polymerase is Taq DNA polymerase. Preferably, the steps of heating, cooling, and incubating the reaction mixture are repeated at least one time. In another preferred embodiment, the DNA product is flanked by the generic sequence and reverse complement of the generic sequence.

A series of DNA amplification reactions are performed with the DNA product, wherein the annealing step is at a temperature that selects for the generic sequence of the second primer hybridizing to complement DNA in the DNA product over the random sequence of the first primer hybridizing to complement DNA in the DNA product. Preferably, the DNA amplification reactions involve a heat-stable DNA polymerase synthesizing a complementary DNA strand from the 3' end of the second primer to produce amplified DNA products. The steps for DNA amplification by the heat-stable DNA polymerase are denaturing the DNA product; annealing the second primer with the DNA product to allow the formation of a DNA-primer hybrid; and incubating the DNA-primer hybrid to allow the heat-stable DNA polymerase to synthesize amplified DNA products. Preferably, the series of DNA amplification reactions includes about 30 to about 35 reactions, and more preferably about 40 reactions. In a preferred embodiment, the products of the DNA amplification reactions are flanked by the generic sequence and reverse complement of the generic sequence.

A preferred embodiment of the present disclosure is a method of amplifying a DNA sample on a solid medium that involves precipitating the DNA sample on the solid medium and subjecting the precipitated DNA to DNA amplification to produce amplified DNA products. Preferably the solid medium is filter paper, and the filter paper is chemically treated. In a preferred embodiment, the DNA sample is dehydrated on the filter paper. In another preferred embodiment, the DNA sample is tissue, and the tissue is blood.

The DNA sample on a solid medium is preferably precipitated with salt and alcohol, and rinsed with alcohol. Preferably, the salt used to precipitated the DNA is sodium acetate, potassium acetate, ammonium acetate, sodium chloride, or potassium chloride; preferably the alcohol used is ethanol or isopropanol. In preferred embodiments, the produced amplified DNA products are subjected to genotype analysis, or a polymorphism is identified in the DNA products, preferably a single nucleotide polymorphism (SNP). The SNP may be identified by a number of techniques well known to those of skill in the art, including preferably DNA sequencing, Oligonucleotide Ligation Assay (OLA), Doublecode OLA, Single Base Extension Assay, allele specific primer extension, or mismatch hybridization.

Another aspect of the present disclosure is a preferred method of identifying a polymorphism, which precipitates a DNA sample on a solid medium, and uses a reaction mixture with the precipitated DNA sample; a first primer with a random sequence of nucleotides at its 3' end and a generic sequence 5' of the random nucleotides; and a second primer with the generic sequence of the first primer and lacking the random sequence of the first primer. In a preferred embodiment, a single reaction mixture is used. Preferably, the reaction mixture also contains other components that are necessary for DNA amplification, which are well known to those of skill in the art. In a preferred embodiment, the amplified DNA products are analyzed to identify a polymorphism, and preferably the polymorphism is a single nucleotide polymorphism (SNP). The methods of identifying SNPs are well known to those of skill in the art. In a preferred embodiment of identifying a SNP, the SNP is identified by DNA sequencing, Oligonucleotide Ligation Assay (OLA), Doublecode OLA, Single Base Extension Assay, allele specific primer extension, or mismatch hybridization.

The DNA sample in the reaction mixture is subjected to DNA amplification by a first DNA polymerase, wherein the first primer anneals to the DNA to allow the first DNA polymerase to synthesize a complementary DNA strand from the 3' end of the first primer to produce a DNA product. The steps for DNA amplification by the first DNA polymerase are denaturing the DNA product; annealing the first primer with the DNA to allow the formation of a DNA-primer hybrid; and incubating the DNA-primer hybrid to allow the first DNA polymerase to synthesize the DNA product. Preferably, these DNA amplification steps are repeated at least one time. In a preferred embodiment, the DNA product produced by the DNA amplification is flanked by the generic sequence and reverse complement of the generic sequence.

This DNA product is then subjected to DNA amplification by a heat-stable DNA polymerase, wherein the second primer anneals to the DNA product to allow the heat-stable DNA polymerase to produce a second DNA product. The second DNA product is produced when the heat-stable DNA polymerase synthesizes a complementary DNA strand from the 3' end of the second primer annealed to the DNA product. The steps for DNA amplification by the heat-stable DNA polymerase are denaturing the DNA product; annealing the second primer with the DNA product to allow the formation of a DNA-primer hybrid; and incubating the DNA-primer hybrid to allow the heat-stable DNA polymerase to synthesize the second DNA product. The amplified DNA product is then preferably analyzed to identify a polymorphism. Preferably, these DNA amplification steps are repeated about 30 to about 35 times, and more preferably about 40 times. In a preferred embodiment, the second DNA product is flanked by the generic sequence and reverse complement of the generic sequence. In another preferred embodiment, the annealing temperature is higher than the optimal annealing temperature of the random sequence of nucleotides at the 3' end of the first primer.

In a preferred embodiment, the solid medium is filter paper, and the filter paper is chemically treated. In another preferred embodiment, the DNA sample is dehydrated on the filter paper. Preferably, the DNA sample is tissue, and the tissue is blood. The DNA sample on a solid medium is preferably precipitated with salt and alcohol, and rinsed with alcohol. Preferably, the salt used to precipitated the DNA is sodium acetate, potassium acetate, ammonium acetate, sodium chloride, or potassium chloride; preferably the alcohol used is ethanol or isopropanol.

The DNA amplification methods of the present disclosure will be useful for amplifying small amounts of DNA, which will allow multiple sites in the DNA sample to be genotyped for high-throughput screening. Additionally, the present method will allow for the rapid construction of band specific painting probes for any chromosomal region, and can also be used to microdissect and amplify unidentifiable chromosomal regions or marker chromosomes in abnormal karyotypes. The presently disclosed method will also allow for the rapid cloning of amplified DNA for sequencing or generating DNA libraries. Thus, the method will not only be a valuable tool for genotype analysis and high-throughput screening, it should also be a valuable tool in cytogenetic diagnosis.

BRIEF DESCRIPTION OF THE SEVERAL VIEWS OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

DETAILED DESCRIPTION OF THE INVENTION

Figure 1:
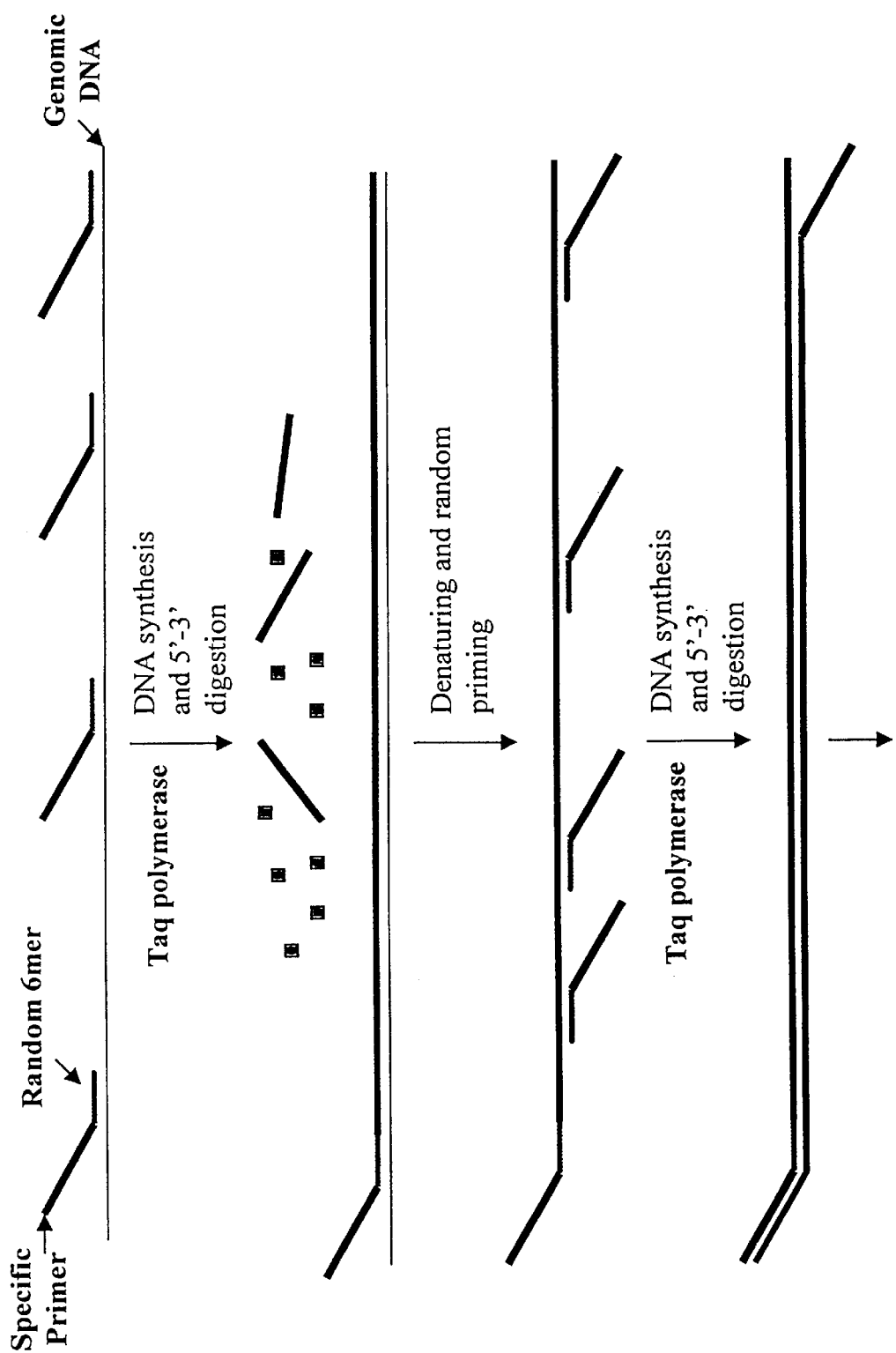
FIG. 1. Diagram to illustrate the first set of reactions of the DNA amplification method. As demonstrated, during the first cycle of DNA amplification the sample DNA is denatured and the first primers randomly prime the single-stranded DNA for DNA synthesis. The specific generic DNA sequence at the 5' end of the first primer does not randomly anneal to the DNA strand. Next, Taq DNA polymerase synthesizes the complementary DNA strand from the 3' end of the randomly annealed first primers. In a second cycle of DNA amplification in the first set of reactions, the newly synthesized DNA strand with the generic sequence at its 5' end is denatured from the sample DNA strand. Next, the first primers again randomly prime the newly synthesized DNA strand, and Taq DNA polymerase synthesizes the complementary DNA strand from the 3' end of the randomly annealed first primers. This results in a final product of a DNA strand flanked by the generic sequence at its 5' end and the reverse complement of the generic sequence at its 3' end. This DNA product will be amplified in a second set of reactions of DNA amplification using a second primer that hybridizes to the generic sequences flanking the DNA products.

Genetic analysis of limited quantities of genomic DNA often occurs in the areas of DNA forensics, paleoarcheology, genetic disease diagnosis, genetic linkage analysis, and genetic diversity analysis. Analysis and research in each of these areas will be greatly improved if an efficient and inexpensive method for amplifying genomic DNA and other types of DNA samples in a sequence-independent matter is available. More extensive genetic analysis of small DNA samples using amplified genomic DNA offers a wide range of benefits in each of the above areas. Additionally, a method that could amplify genomic DNA from a single cell, either haploid or diploid, would allow for a more complete genetic analysis of an individual cell from, for example, a pre-implantation embryo, fetal cells in the peripheral blood of pregnant women, sperm, or oocytes. The methods of DNA amplification set forth in the present disclosure can be utilized in any of the above areas to amplify DNA from limited starting materials, thereby allowing for more complete genetic analyses of a large range of DNA samples. Additionally, these methods are practical for wide-scale, high-throughput screening of DNA samples.

Those of skill in the art understand that the basic steps in DNA amplification are heat denaturation, annealing of oligonucleotide primers, and extension of complementary DNA by a DNA polymerase. The steps of denaturation, annealing, and extension make up a single cycle of DNA amplification. In the heat denaturation step, the temperature is raised to a temperature sufficient to cause double-stranded DNA to denature into single-stranded DNA. Next, during the annealing step, the temperature is lowered to a temperature that facilitates the annealing of the oligonucleotide primers to the single-stranded DNA. Finally, during extension, the incubation temperature allows the DNA polymerase to synthesize complementary DNA from the 3' end of the annealed primer. In the presently disclosed methods for DNA amplification, the sample DNA, a first primer having random nucleotides at its 3' end and a generic sequence at its 5' end, and a second primer with the generic sequence of the first primer are placed together in a single reaction mixture. The sample DNA is then amplified using a first set of reactions and a second set of reactions, each of which includes the steps of denaturation, annealing, and extension.

The first set of reactions of DNA amplification begins by denaturing the double-stranded DNA sample to a single-stranded condition, which allows primers to anneal to the DNA. Next, the reaction temperature is lowered to a temperature that allows the random nucleotides at the 3' end of the first primer to anneal to the DNA to form hybrid duplexes. After the hybrid duplexes form, DNA polymerase present in the reaction mixture extends the complementary DNA strand from the 3' end of the first primer during an incubation period. The DNA polymerase will preferably have 5' to 3' exonuclease activity so that it will be able to remove other first primers annealed further downstream on the same DNA strand, thus allowing longer complementary DNA strands to be synthesized during the first set of reactions. Alternatively, the DNA polymerase can have primer displacement activity, which will achieve a similar result. Primer displacement activity means that when the DNA polymerase is moving along the DNA strand synthesizing complementary DNA and it encounters another primer annealed to the DNA, the primer will be displaced and the polymerase reaction will proceed. This activity also results in longer polymerization products. While the annealing and incubation steps are preferably performed at different temperatures, both the annealing and incubation steps may occur at the same temperature if the DNA polymerase is active at that temperature in the first set of reactions.

After the first cycle of DNA amplification described above, the newly synthesized complementary DNA strand will have the generic sequence of the first primer at its 5' end, which was incorporated into the strand when the 3' end of the first primer was used as the starting point for synthesizing the complementary DNA strand (see FIG. 1.). The above steps of denaturation, annealing, and extension can be repeated, and generally should be repeated at least once during the first set of reactions. The denaturation step of the second cycle of the first set of reactions separates the new first cycle DNA strands with the 5' generic sequence from the original DNA strands. After denaturation, the new first cycle DNA strands are available to the first primer present in the reaction mixture for another round of annealing and extension.

During the second cycle of the first set of reactions, the first primer anneals to the first cycle DNA strand, DNA polymerase extends a complementary strand from the 3' end of the first primer, and the newly synthesized complementary DNA once again incorporates the 5' end of the first primer into its sequence. This new second cycle DNA fragment will also have the reverse complement of the generic sequence on its 3' end, because DNA polymerase will synthesize the full-length complementary DNA product of the first cycle DNA strand, which has the generic sequence at its 5' end. Thus, the DNA fragments amplified during the first set of reactions have the generic sequence at one end of the fragment and its reverse complement at the other. These DNA products of the first set of reactions flanked with the generic sequence and its reverse complement can now be readily amplified during a second set of reactions with a second primer. The second primer has the same generic DNA sequence as the first primer, but without the random nucleotides at its 3' end.

The DNA products of the first set of reactions are subsequently amplified using the second primer present in the single reaction mixture. After these DNA products are denatured, the temperature of the reaction is lowered so that the second primer will anneal to the generic sequence at the ends of the DNA products. The annealing temperature used for the second set of reactions will generally be higher than the annealing temperature used in the first set of reactions. The annealing temperature used in the second set of reactions should be higher than the optimal annealing temperature of the random sequence of the nucleotides of the first primer. The higher temperature will minimize or prevent random priming by the first primer through its random nucleotide sequence located at its 3' end in the second set of reactions. This characteristic eliminates the need to remove any remaining first primer from the single reaction mixture during the second set of reactions.

After the second primer anneals to the ends of the DNA products, a heat-stable DNA polymerase extends the complementary DNA strand from the 3' end of the second primer. The second set of reactions involves repeating the above steps of denaturation, annealing, and extension to achieve exponential amplification of the DNA products, preferably using a total of about 30 to about 40 cycles. The final amplified DNA is ready for extensive analysis using a variety of techniques, such as utilizing the amplified DNA to genotype multiple sites in the DNA, including polymorphisms such as SNPs, single tandem repeats (STRs), restriction fragment length polymorphisms (RFLPs), variable number of tandem repeats (VNTRs), complex tandem repeats (CTRs), microsatellites, deletions, substitutions, or insertions. Alternatively, the amplified DNA may be used to generate DNA libraries from a variety of sources.

Any type of DNA sample may be amplified using the methods of the present disclosure because it is a sequence-independent method of DNA amplification that can amplify even trace amounts of DNA. In one preferred embodiment, the DNA sample is genomic DNA, microdissected chromosome DNA, yeast artificial chromosome (YAC) DNA, P1 derived artificial chromosome (PAC) DNA, cosmid DNA, phage DNA, or bacterial artificial chromosome (BAC) DNA. In another preferred embodiment, the DNA sample is tissue, blood, or a single cell. Preferably the DNA sample is readily and easily obtained from an organism, and is easy to store. The DNA sample can be obtained from any species or organism, including but not limited to human, mammal, bovine, porcine, ovine, equine, rodent, avian, fish, zebrafish, shrimp, plants, yeast, virus, or bacteria.

DNA samples of tissue or blood containing genomic DNA suitable for DNA amplification by the disclosed method may be conveniently obtained from, for example, buccal swab, nose swab, hair, mouthwash, cord blood, amniotic fluid, embryonic tissue, endothelial cells, hoof clippings, or fingernail clipping. Genomic DNA in paraffin-embedded tissue may also be amplified using the disclosed method. The DNA amplification methods of the present disclosure can amplify genomic DNA from a single cell, including but not limited to a single cell isolated from a pre-implantation embryo, fetal cells in the peripheral blood of pregnant women, sperm, or oocytes, or a single cell from any tissue. A single cell may be isolated using a variety of methods, including flow cytometry (Herzenberg et al., *Proc Natl Acad Sci USA* 76:1453–55,1979; Iverson et al., *Prenatal Diagnosis* 1:61–73, 1981; Bianchi et al., *Prenatal Diagnosis* 11:523–28, 1991), which can utilize fluorescent activation cell sorting (FACS), magnetic-activated cell sorting (MACS, Ganshirt-Ahlert et al., *Am J Obstet Gynecol* 166:1350, 1992), or a combination of both procedures. Additionally, a combination of gradient centrifugation and flow cytometry methods can also be used to increase isolation or sorting efficiency. In one preferred embodiment, the DNA sample does not have to be purified or treated with proteinase K before DNA amplification using the disclosed method.

The first primer used in the DNA amplification methods of the present disclosure preferably has about 4 to about 9 random nucleotides at its 3' end. In a preferred embodiment, the first primer has 5, 6, 7, or 8 random nucleotides at its 3' end. The first primer also has from about 10 to about 30 and preferably from about 15 to about 25 nucleotides of a generic sequence at its 5' end. In a preferred embodiment the first primer has 16, 17, 18, 19, 20, 21, 22, 23, or 24 nucleotides of a generic sequence at its 5' end. The random sequence of nucleotides and the generic sequence 5' of the random nucleotides may be adjacent in the first primer. Alternatively, one or more nucleotides may be inserted between the random sequence of nucleotides and the generic sequence 5' of the random nucleotides in the first primer. The first primer may also have additional nucleotides 5' of the generic sequence. An example of a first primer is the sequence designated SEQ ID NO: 1, in which N designates a random nucleotide. The random sequence of nucleotides can be composed of any of the nucleotides, for example G, A, T, or C, in any order. It is understood that these letter designations represent G for guanine, A for adenine, T for thymine, and C for cytosine nucleotides. The random nucleotides can also include nucleotide analogs, and other modified nucleotides that are well known to those of skill in the art.

The first primer theoretically may contain all combinations of these nucleotides in every position of the random portion of the primer. Thus, the random nucleotides at the 3' end of the first primer will be complementary to random sites throughout the target DNA segments. It is understood by those of skill in the art that the longer the random sequence of nucleotides is in the first primer the less often the target sequence will occur in the genome, and therefore the less often the first primer will anneal to the target DNA segments. Additionally, the random sequence of the first primer can be designed to be rich in the nucleotides A and T or alternatively in the nucleotides G and C to allow for preferential amplification of particular regions in the sample DNA, such as A:T rich regions or G:C rich regions. It is well within the skill of those in the art to use any ratio of the 4 nucleotides to generate the random sequence of nucleotides.

As an example, if the 3' end of the first primer has 5 random nucleotides, there would be $4^5$ or 1,024 different sequences in the random segment of the first primer for that particular amplification. The complements of these sequences occur in both orientations at random throughout the denatured DNA segments of the DNA sample. By both orientations it is meant that priming would occur on both strands of the melted DNA duplex that is to be amplified.

As used herein, the term "generic sequence" refers to any DNA sequence that would be a useful DNA amplification primer. An example of the second primer is the sequence designated SEQ ID NO:2. Thus, the generic sequence will preferably not have any obvious self-homologies, nor runs of the same nucleotide, and the generic sequence is preferably not overly G:C or A:T rich. A primer that contains self-homologies or sequences in one region that are complementary to sequences in another region of the primer will form internal hairpin duplexes and thus would be unavailable to hybridize with the sample DNA. Also, since G:C pairing involves 3 hydrogen bonds and A:T pairing involves 2 hydrogen bonds, a primer with a disproportionately high content of the nucleotides G or C, singly or in combination, will have a higher melting temperature than a primer that was comprised of a higher content of A and T. One of skill in the art can use this characteristic to manipulate the annealing temperatures of the first and second primers to a higher or lower temperature in the disclosed DNA amplification method. Within the limits mentioned above, any generic sequence that can be used to amplify DNA using the disclosed method is contemplated to be within the scope of the present disclosure.

The sequence of the second primer used in the second set of reactions is the same as the generic nucleotide sequence 5' of the random nucleotide sequence of the first primer. While the second primer may have additional nucleotides at its 5' end, this will affect the annealing temperature of the DNA amplification reaction. The second primer may also have additional nucleotides at its 3' end, but these may interfere with the ability of the primer to uniformly amplify DNA products during the second set of reactions of DNA amplification by reducing the ability of the second primer to universally bind and amplify the DNA products of the first set of reactions. Therefore, the second primer will preferably have no additional nucleotides on its 3' end.

In the first set of reactions of the disclosed method as described in the paragraphs above, lower temperatures for the annealing reaction are used because the first primer anneals to the sample DNA through a short sequence of random nucleotides at its 3' end. The incubation temperature preferably will allow for DNA polymerase to successfully synthesize the complementary DNA strand from the 3' end of the annealed primer. If Taq DNA polymerase is used in the first set of reactions, an extension temperature that allows Taq to have polymerase activity should be used. The DNA products of this first set of reactions are flanked by the generic sequence of the first primer and its reverse complement.

During the second set of reactions of DNA amplification, the second primer will hybridize to these flanking sequences. Because the generic DNA sequence is longer than the stretch of random nucleotides at the 3' end of the first primer, the annealing temperature in the second set of reactions will generally be at a higher temperature. The higher annealing temperature will generally minimize or prevent any remaining first primers that were not incorporated into DNA products of the first set of reactions but are still present in the reaction mixture from annealing to the DNA products and randomly initiating DNA synthesis. Higher temperatures generally require the use of a polymerase that is heat-stable, which means that the polymerase can synthesize DNA at high temperatures. One well-known example of a heat-stable DNA polymerase is Taq DNA polymerase. A number of heat-stable or thermostable DNA polymerases are commercially available, including recombinant Taq DNA polymerases and native Taq DNA polymerases (see Table 2). Another option is to use long-range PCR to generate longer DNA products with, for example, TaqPlus DNA Polymerase. Long-range PCR can be used in either the first set of reactions, the second set of reactions, or both sets of reactions. In one embodiment, Tub DNA polymerase can be used to amplify long DNA sequences in the presently disclosed DNA amplification method. Protocols for using Tub DNA polymerase and amplifying long regions of DNA are found in Forrester and Redford (*Methods Mol. Biol.* 67:31–38, 1997), incorporated herein by reference.

In the presently disclosed method, the DNA to be amplified in the first set of reactions is first denatured by heating the reaction mixture to between about 90° C. and about 100° C., and preferably to about 95° C. for about one to about five minutes and preferably for about two minutes. During this step, both the first and second primers are present in the reaction mixture. Alternatively, the second primer may be added to the reaction mixture after the first set of reactions but before the second set of reactions. The first and second primers can be added to the reaction mixture containing the DNA sample to be amplified before heat denaturation or at any time during the denaturation step of the first cycle of the first set of reactions. In the preferred embodiment, the first and second primers are added to the single reaction mixture in equal molar ratios. The molar ratios of the two primers, however, may also vary in relation to each other to optimize DNA amplification. The molar ratios of the DNA to be amplified and the first and second primers can be varied by one of skill in the art to optimize DNA amplification.

Next, the temperature of the reaction mixture is lowered to a temperature that allows the first primer to anneal to the single-stranded DNA. The second primer present in the reaction mixture will not generally anneal to the single-stranded DNA in the first set of reactions because the reverse complement of the longer generic DNA sequence necessary for annealing the primer will rarely, if at all, be present in the single-stranded DNA. The annealing temperature of the random sequence of nucleotides of the first primer preferably should be between about 37° C. and about 50° C., preferably between about 42° C. and about 45° C. Preferably, a different temperature from the annealing temperature may be used during the incubation period for extension of the complementary DNA strand that allows the DNA polymerase to synthesize DNA from the 3' end of the first primer. If the DNA polymerase functions at the annealing temperature, then this temperature may be maintained during the incubation period. The incubation period is preferably about 2 minutes to about 7 minutes, more preferably about 5 minutes.

These steps of the first set of reactions should be repeated at least once, so that preferably two cycles of these initial DNA amplification steps are performed, although more than two cycles of DNA amplification in this first set of reactions is contemplated. For example, 3 or 4 cycles may be performed in the first set of reactions. But for every additional cycle of denaturation, annealing, and extension, the DNA products available for the second set of reactions of DNA amplification will generally be shortened. This is because each successive round of random priming by the first primer further shortens the previously amplified DNA products. This effect is overcome during the second set of reactions of DNA amplification because the second primers anneal to the ends of the DNA products flanked by the generic sequence and the reverse complement of the generic sequence produced in the first set of reactions.

The DNA products of the first set of reactions, which are flanked by the generic sequence and its reverse complement are subsequently exponentially amplified in the second set of reactions of DNA amplification in the disclosed method. In the second set of reactions, the DNA products of the first set of reactions are first denatured by heating the reaction mixture to between about 90° C. and about 100° C., and preferably to about 95° C. for about 15 seconds to about 2 minutes, preferably for about 30 seconds to about 1 minute. Next, the temperature of the reaction mixture is decreased to a temperature that allows the second primer to anneal to the single stranded DNA products. The annealing temperature of the second primer is preferably between about 55° C. and about 68° C., preferably between about 60° C. and about 65° C. The annealing temperature of the second primer must be stringent enough to minimize or prevent random priming by the unincorporated first primers remaining in the reaction mixture. Therefore, it is not necessary to remove the first primers from the reaction mixture during the second set of reactions, which increases the efficiency of the disclosed method. This also greatly simplifies the present DNA amplification method for high-throughput screening as compared to other known methods.

While the incubation temperature may be the same as the annealing temperature in the second set of reactions if the DNA polymerase is active at that temperature, preferably the temperature of the incubation step is raised to a more optimal temperature for the heat-stable DNA polymerase to synthesize DNA. The optimal temperature for the extension step will be dependent on the DNA polymerase used in the second set of reactions. For example, during the incubation step of the second set of reactions, the temperature is increased to about 68° C. to about 75° C., and preferably to about 70° C. to about 72° C., and held for about 30 seconds to about 10 minutes, and preferably for about 4 minutes to about 6 minutes. The denaturation, annealing, and extension steps of the second set of reactions are repeated about 30 to about 40 times, and preferably about 33 to about 35 times. The reaction can then be held at about 720 C for about 7 minutes to about 10 minutes to complete any nascent polymerizations. It is not necessary to add fresh enzyme after each denaturation step if a heat-stable DNA polymerase such as the Taq DNA polymerase is used because Taq is not completely denatured by the denaturation step, and functions optimally at higher temperatures. Although a non-heat-stable DNA polymerase could also be used in the second set of reactions if it were added after each denaturation step of every cycle, this inefficient method would be impractical for high-throughput screening.

It is well known to those of skill in the art that the optimal temperatures for each step of the first set of reactions and the second set of reactions are determined (usually empirically) by the size of the sample DNA to be amplified and by the size and sequence of the primers. For example, simple formulas for determining the melting temperature of a perfectly matched duplex based on the G:C content of the primer are well known in the art. The optimal annealing temperature of a primer can be calculated by one of skill in the art by using a variety of available computer software programs, such as Oligo Analyzer, which is available at the website www.idtdna.com. It is also well known to one of skill in the art that the temperatures between any of the steps in the first set of reactions and/or the second set of reactions may be increased or decreased gradually over about a 1 to about an 8 minute period of time, and preferably over about a 3 minute period of time.

One of skill in the art may also desire to incorporate one or more restriction enzyme sites in the generic sequence for subsequent cloning of the amplified products. Restriction enzymes sites are DNA sequences that are recognized and cleaved at a specific point by a restriction endonuclease enzyme. The use of particular restriction enzymes is well known in the art (see Table 1), and a particular restriction enzyme compatible with the vector of choice for cloning the amplified DNA may be chosen. The number of available vectors are too numerous to list, and are well known to those of skill in the art. Popular vectors such as pBR322, or the pGem or PUC series of plasmids, contain certain specific restriction enzyme recognition sites in their polyclonal regions. The generic sequence can be designed so that one or more recognition sequences are included in the generic primer that are compatible with sites in the chosen cloning vector.

In a certain embodiment, the present disclosure encompasses a first primer and a second primer for use in DNA amplification. The first primer preferably has a region of about 4 to about 8 random nucleotides at its 3' end and about 15 to about 25 bp of a generic DNA 5' of the random nucleotide sequence. This first primer is further characterized by the ability of its random sequence of nucleotides to hybridize to DNA sequences at a temperature of between about 37° C. and about 42° C. The second primer is preferably between about 15 and about 25 bp in length, and has the same sequence as the generic sequence 5' of the random sequence of nucleotides in the first primer. The second primer may also have additional nucleotides to facilitate the method of DNA amplification, particularly in relation to the high stringency annealing step in the second set of reactions. The second primer can further contain a restriction enzyme recognition site to facilitate the subcloning of the amplified DNA products into a vector of choice or a stretch of CUA repeats to facilitate cloning, for example by the "Clone Amp" protocol (BRL).

In a preferred embodiment, the DNA polymerase used to amplify the DNA in the first set of reactions is the same as the heat-stable DNA polymerase used in the second set of reactions. Using the same DNA polymerase for both the first and second set of reactions greatly simplifies the disclosed method of DNA amplification because only one reaction mixture is prepared with the single heat-stable DNA polymerase, which greatly facilitates high-throughput screening. Using the same DNA polymerase means that the enzyme is simply added to the initial reaction mixture, and no additional enzyme must be added during the first or second set of reactions of DNA amplification.

It is also contemplated, however, that one DNA polymerase may be used in the first set of reactions and a second heat-stable DNA polymerase used in the second set of reactions. During the first set of reactions, if a heat-stable DNA polymerase is not used, fresh enzyme must be added to the reaction mixture after each denaturation step, because the DNA polymerase will be destroyed by the heat necessary to denature the DNA. The DNA amplification steps of the first set of reactions are repeated one to three times, preferably one time as discussed above, again with fresh enzyme added after each denaturation step. A heat-stable DNA polymerase must then be added for the second set of reactions of DNA amplification, either before, during or after the first denaturation step of the second set of reactions.

The preferred DNA polymerase used in the presently disclosed method is a heat-stable enzyme with 5' to 3' exonuclease activity, or alternatively primer displacement activity. For example, Taq DNA polymerase can be added to the initial reaction mixture to amplify the DNA in both the first set of reactions and the second set of reactions of the disclosed method. Taq DNA polymerase possesses intrinsic 5' to 3' exonuclease activity, which allows Taq to digest oligonucleotide primers that it encounters downstream while synthesizing complementary DNA (Longley et al., *Nucleic Acids Res* 18(24):7317–22, 1990). DNA polymerases that may be used in the first set of reactions include any polymerase with 5' to 3' exonuclease activity, or alternatively primer displacement activity with or without exonuclease activity. Enzymes that may be used in the first set of reactions include but are not limited to, Taq DNA polymerase, modified Taq DNA polymerase such as for example Amplitaq Gold, *E.coli* DNA Polymerase I, Tub DNA Polymerase, and DNA Polymerase I (see Table 2).

If the DNA polymerase used in the first set of reactions differs from the heat-stable DNA polymerase used in the second set of reactions, the final DNA products of the first set of reactions may have to be diluted into buffer that allows the heat-stable DNA polymerase to perform optimally. The first set of reactions may be performed in relatively low volume, particularly when the sample DNA is present in small amounts as in microdissected chromosomes and in YACs isolated from pulsed field gels, or from small tissue or blood samples, or single cells. It is contemplated that the volume of the first set of reactions and the second set of reactions may vary widely depending on the particular application and that higher or lower reaction volumes are encompassed by the present disclosure. Although a small aliquot of the first set of reactions may be used with a heat-stable DNA polymerase and its buffer in the second set of reactions, preferably the reaction volume for both the first set of reactions and second set of reactions is the same, particularly if the same DNA polymerase is utilized for both sets of reactions.

It is contemplated that when DNA polymerase and its buffer are added to the single reaction mixture of the present method, other components necessary for DNA amplification are present in the reaction mixture. The necessary reaction components for DNA amplification are well known to those of skill in the art and may include, but are not limited to, bovine serum albumin, $MgCl_2$ in a concentration of about 1.5 mM to about 5 mM final concentration, the four deoxynucleotide bases (dATP, dGTP, dTTP, and dCTP), and purified water, for example distilled, deionized or ultrafiltered water. The buffers employed may contain components such as Tris HCl at a pH of about 7.0 to about 9.0, $MgCl_2$, NaCl, and DTT (dithiothreitol). Buffers may also include KCl and gelatin. The composition of buffers for PCR and DNA amplification are well known to those of skill in the art, and the concentration of certain components such as $MgCl_2$ for example, can easily be determined empirically for each reaction.

It is also understood by those of skill in the art that the temperatures, incubation periods, and ramp times of the DNA amplification steps may vary considerably without significantly altering the efficiency of DNA amplification and other results. Alternatively, those of skill in the art may alter these parameters to optimize the DNA amplification reactions. These minor variations in reaction conditions and parameters are included within the scope of the present disclosure. The DNA products of the above reactions may be visualized by running them on an agarose or acrylamide electrophoresis gel, preferably on a 1.5% to 2.0% agarose gel. After staining the gel with ethidium bromide, the products of the random, sequence independent amplification will preferably appear as a smear.

In one embodiment, the present disclosure encompasses a method for amplifying DNA, independent of the sequence of the DNA, that includes the steps of:

(a) adding to the DNA sample in a single reaction mixture, 10 mM Tris HCl (pH 8.3), 5 mM $MgCl_2$, 50 mM KCl, 0.001% gelatin, 300 µM dNTP (dATP, dGTP, dCTP, and dTTP), 300 nM of the first primer having the sequence of SEQ ID NO:1, 300 nM of the second primer having the sequence of SEQ ID NO:2, and 1.25 unit Taq DNA polymerase, for a total volume of about 50 µM;

(b) denaturing the DNA by heating the reaction mixture to a temperature of about 95° C. for about 5 minutes;

(c) denaturing the DNA by heating the reaction mixture to a temperature of about 95° C. for about 1 minute, and then cooling the reaction mixture to a temperature of about 42° C. for about 5 minutes, thereby allowing the first primer to anneal to the denatured DNA to form a DNA-primer hybrid and the Taq DNA polymerase to synthesize the complementary strand of DNA from the 3' end of the first primer;

(d) repeating step (c) one time;

(e) denaturing the DNA products by heating the reaction mixture to a temperature of about 95° C. for about 15 seconds, cooling the reaction mixture to a temperature of about 65° C., thereby allowing the second primer to anneal to the denatured DNA to form a DNA-primer hybrid; and raising the reaction mixture to a temperature of about 68° C., thereby allowing the Taq DNA polymerase to synthesize the complementary strand of DNA from the 3' end of the second primer;

(f) repeating step (e) about 39 times.

An example of the first primer is the sequence 5'-TAGCAGTGGTAACAACGCAGAGANNNNN-3' (SEQ ID NO:1). An example of the second primer is the sequence 5'-TAGCAGTGGTAACAACGCAGAGA-3' (SEQ ID NO:2). Additional examples of the generic sequence that may be used as a second primer in the presently disclosed method to amplify DNA include, but are not limited to:

5'-ACAACGCAGAGTAAGCAGTGGTA-3', SEQ ID NO:3;

5'-ACAACGGTAGCAGAGTAAGCAGT-3', SEQ ID NO:4;

5'-GAGTAAGCAGTACAACGGTAGCA-3', SEQ ID NO:5;

5'-GAGGCATAAGCAGTACAACGGTA-3', SEQ ID NO:6;

5'-CAACGGTAGAGGCATAAGCAGTA-3', SEQ ID NO:7;

5'-GGCATAAGCAGTACAACGGTAGA-3', SEQ ID NO:8;

5'-AACGGTAGAGGCATAAGCAGTAC-3', SEQ ID NO:9;

5'-AGTACAACGGTAGAGGCATAAGC-3', SEQ ID NO:10;

5'-AAGCAGTACAACGGTAGAGGCAT-3', SEQ ID NO:11;

5'-CGGTAGAGGCATAAGCAGTACAA-3', SEQ ID NO:12.

The first primer used in the same reaction mixture for DNA amplification with each of the above second primers will contain the same generic sequence with an additional random sequence of nucleotides at its 3' end. The optimal annealing temperatures of the first set of reactions and the second set of reactions of DNA amplification can be determined by one of skill in the art based on the generic DNA sequence and the number of random nucleotides at the 3' end of the first primer. Preferably, the optimal annealing temperature of each set of reactions will be such that second primer annealing is minimized or prevented in the first set of reactions and first primer annealing through its random sequence of nucleotides is minimized or prevented in the second set of reactions.

When DNA samples utilized in the presently disclosed DNA amplification methods are stored on a solid medium, preparing the DNA sample for amplification and/or genetic analysis can be not only inefficient, but also can yield inconsistent results, thereby limiting the information that is obtained from the DNA sample. The present disclosure seeks to overcome the drawbacks inherent in other methods of preparing DNA samples stored on solid mediums for DNA amplification and/or genetic analysis. The presently disclosed method, also termed the precipitation method, greatly simplifies the preparation of DNA samples stored on a solid medium by eliminating the unnecessary steps of DNA purification. In the disclosed method, the DNA sample on a solid medium is precipitated by methods well known to those of skill in the art, and then directly subjected to DNA amplification and/or genetic analysis. This method produces more consistent results, reduces the cost of high-throughput operations, and improves the quality of DNA amplified from the DNA sample.

The present disclosure includes the variety of solid mediums well known to those of skill in the art for storing DNA, including as tissue and blood samples. Preferably, the solid medium is dry, and has a solid matrix or solid support, such as preferably an absorbent cellulose-based paper (such as filter paper), or a micromesh of synthetic plastics materials. The solid matrix may also be in the form of a tablet or pellet. Preferably the solid medium will protect against the degradation of the DNA sample incorporated or absorbed on the matrix or support. A solid medium allows DNA samples to be stored and transported in a form suitable for the recovery of the DNA in the sample for genotype analysis. DNA samples can be collected and stored for example on FTA™ paper, Whatmann® paper, Gibson paper, Guthrie cards, swabs, and filter paper. In a preferred embodiment the DNA sample is stored on FTA paper. Blood or tissue collected on filter paper can be dried and stored at room temperature.

Methods of precipitating DNA using a salt and alcohol solution are well known to those of skill in the art, and are included within the scope of the present disclosure. In a preferred embodiment, the precipitation method of the present disclosure begins by washing the DNA sample on the solid medium with water, for example distilled, deionized, or ultrafiltered water, to remove any chemicals that might interfere with subsequent DNA amplification reactions. In a preferred embodiment, the DNA sample is repeatedly washed with water. Next, the solid medium is treated with a solution that includes salt and alcohol, which precipitates the DNA in the sample. After the precipitation step the DNA is fixed on the solid support. In a preferred embodiment, the salt used to precipitate the DNA is sodium acetate, potassium acetate, or ammonium acetate, preferably at a concentration of about 0.1 to about 0.5 M, more preferably about 0.2 to about 0.3 M. In another preferred embodiment, the alcohol used to precipitate the DNA is isopropanol, ethanol, or other similar water-miscible solvents such as n-propanol, preferably at a purity level of about 70% to about 100%, more preferably about 95%. It is well within the skill of those in the art to determine the appropriate ratio of salt to alcohol in the precipitation solution to precipitate the DNA. In a preferred embodiment, the ratio is 50/50 v/v.

After the DNA is precipitated, it is washed with alcohol to dissolve any salts remaining in the sample from the precipitation step. This step can also accelerate dehydration of the sample. In a preferred embodiment, the alcohol used to wash the precipitated DNA is isopropanol, ethanol, or other similar water-miscible solvents such as n-propanol, preferably at a purity level of about 80% to about 95%, more preferably about 70%. Interestingly, when DNA samples on FTA paper are processed using the disclosed precipitation method, the final DNA-paper can remain the red-brown color of blood. Nevertheless, the processed DNA on the FTA paper now can be efficiently and predictably amplified by any one of many methods of DNA amplification known by those of skill in the art, including but not limited to the DNA amplification method of the present disclosure, as well as PCR™. Thus, the presently disclosed methods greatly reduce the variation of DNA amplification efficiency found when DNA samples stored on solid supports are processed using commercially available reagents.

Additionally, the solutions used in the presently disclosed precipitation method, which include water, alcohol, and salts, are inexpensive and easy to make. The disclosed precipitation method thus also greatly reduces the cost of high-throughput operations, particularly when compared to other commercially available reagents. For example, the ethanol wash can reduce the time for FTA paper dehydration by at least 50% when compared to the water-based FTA Purification Reagent protocol. Additionally, the presently disclosed methods for precipitation and DNA amplification to analyze DNA samples stored on FTA paper can all be conducted in 96-well or 384-well plates, which greatly facilitates high-throughput operations.

Genotype analysis of sample DNA on a solid support, processed using the disclosed precipitation and/or DNA amplification methods, or genotype analysis of DNA amplified by the preferred methods of the present disclosure, may be performed using a variety of methods and techniques that are well known to those of skill in the art. The advantages offered by the disclosed methods of DNA amplification for high-throughput screening are that the genotypes of large numbers of organisms can be rapidly screened for diagnostic or research purposes. The term "genotype analysis" refers to any type of genetic typing, genotyping, fingerprinting, haplotyping, DNA typing, or any similar phrase. The term includes the use of any methods or protocols known to those of skill in the art for determining an individual's genotype at one or more genetic loci, including identifying haplotypes. Techniques that are nucleic acid based include but are not limited to size fractionation, SNP analysis, allele specific oligonucleotide (ASO) hybridization, sequencing, RFLP analysis, denaturation temperature analysis, and mass spectrometry analysis.

Methodologies available to those of skill in the art are numerous and continually developing, and cannot be detailed herein. Many types of polymorphisms may be detected using amplified DNA, including but not limited to SNPs, RFLPs, VNTRs, STRs, CTRs, and microsatellites.

Single nucleotide polymorphisms (SNPs) are nucleotide sequence variants that are of predictive value in identifying many genetic diseases, as well as phenotypic characteristics that may be desirable, which are often caused by a limited number of different mutations in a population. SNPs are found in both coding and non-coding regions of genomic DNA. In spite of the paucity of scorable phenotypes, SNPs are found in large numbers throughout the human genome (Cooper et al., *Hum Genet* 69:201–205, 1985). Certain SNPs result in disease-causing mutations such as, for example, heritable breast cancer (Cannon-Albright and Skolnick, *Semin Oncol* 23:1–5, 1996). It is specifically contemplated that DNA amplified by the disclosed methods may be useful in the detection of SNPs or other polymorphisms in an individual. Current methods of screening for polymorphisms are known (see for example U.S. Pat. Nos. 6,221,592 and 5,679,524). A limitation of these techniques, however, is the inability to provide multiple copies of genomic DNA to enhance signals and facilitate detection. The disclosed methods overcome this problem by facilitating rapid, high-throughput DNA amplification of randomly primed nucleic acid sequences throughout the full length of, for example, an individual's genome. Since multiple copies of each region including a SNP or other polymorphism would be present in a sample following DNA amplification using the disclosed methods, the likelihood of producing a detectable signal utilizing standard SNP detection methods increases.

A SNP may be identified in the DNA of an organism by a number of methods well known to those of skill in the art, including but not limited to identifying the SNP by PCR™ or DNA amplification, Oligonucleotide Ligation Assay (OLA) (Landegren et al., *Science* 241:1077, 1988), Double-code OLA, mismatch hybridization, mass spectrometry, Single Base Extension Assay, RFLP detection based on allele-specific restriction-endonuclease cleavage (Kan and Dozy, *Lancet* ii:910–912, 1978), hybridization with allele-specific oligonucleotide probes (Wallace et al., *Nucl Acids Res* 6:3543–3557, 1978), including immobilized oligonucleotides (Saiki et al., *Proc Natl Acad Sci USA* 86:6230–6234, 1989) or oligonucleotide arrays (Maskos and Southern, *Nucl Acids Res* 21:2269–2270, 1993), allele-specific PCR™ (Newton et al., *Nucl Acids Res* 17:2503–16, 1989), mismatch-repair detection (MRD) (Faham and Cox, *Genome Res* 5:474–482,1995), binding of MutS protein (Wagner et al., *Nucl Acids Res* 23:3944–3948, 1995), single-strand-conformation-polymorphism detection (Orita et al., *Genomics* 5:874–879, 1983), RNAase cleavage at mismatched base-pairs (Myers et al., *Science* 230:1242, 1985), chemical (Cotton et al., *Proc Natl Acad Sci USA* 85:4397–4401, 1988) or enzymatic (Youil et al., *Proc Natl Acad Sci USA* 92:87–91, 1995) cleavage of heteroduplex DNA, methods based on allele specific primer extension (Syvanen et al., *Genomics* 8:684–692, 1990), genetic bit analysis (GBA) (Nikiforov et al., *Nuci Acids Res* 22:4167–4175, 1994), and radioactive and/or fluorescent DNA sequencing using standard procedures well known in the art.

Preferably the identified SNP is linked to a phenotype, including disease phenotypes and desirable phenotypic traits. The amplified DNA products of the disclosed methods may also be used to generate a DNA library, including genomic DNA libraries, particularly if the generic sequence of the first and second primers include a restriction enzyme site to facilitate cloning of the DNA products. Additionally, the presently disclosed methods allow for the rapid construction of band specific painting probes for any chromosomal region, and can also be used to microdissect and amplify unidentifiable chromosomal regions or marker chromosomes in abnormal karyotypes. Thus, the disclosed methods are not only a valuable tool for genotype analysis and high-throughput screening, but also a valuable tool in cytogenetic diagnosis.

A Single Base Extension Assay is performed by annealing an oligonucleotide primer to a complementary nucleic acid, and extending the 3' end of the annealed primer with a chain terminating nucleotide that is added in a template directed reaction catalyzed by a DNA polymerase. The selectivity and sensitivity of a single base primer extension reaction are affected by the length of the oligonucleotide primer and the reaction conditions (e.g. annealing temperature, salt concentration). The selectivity of a primer extension reaction reflects the amount of exact complementary hybridization between an oligonucleotide primer and a nucleic acid in a sample. A highly selective reaction promotes primer hybridization only to nucleic acids with an exact complementary sequence (i.e. there are no base mismatches between the hybridized primer and nucleic acid). In contrast, in a non selective reaction, the primer also hybridizes to nucleic acids with a partial complementary sequence (i.e. there are base mismatches between the hybridized primer and nucleic acid). In general, parameters which favor selective primer hybridization (for example shorter primers and higher annealing temperatures) result in a lower level of hybridized primer. Therefore, parameters which favor a selective single base primer extension assay result in decreased sensitivity of the assay.

Additionally, cycled Single Base Extension Reactions may be performed by annealing a nucleic acid primer immediately 5' to a region containing a single base to be detected. Two separate reactions are conducted. In the first reaction, a primer is annealed to the complementary nucleic acid, and labeled nucleic acids complementary to non-wild-type variants at the single base to be detected, and unlabeled dideoxy nucleic acids complementary to the wild-type base, are combined. Primer extension is stopped the first time a base is added to the primer. Presence of label in the extended primer is indicative of the presence of a non-wild-type variant. A DNA polymerase, such as Sequenase™ (Amersham), is used for primer extension. In a preferred embodiment, a thermostable polymerase, such as Taq or thermal sequenase is used to allow more efficient cycling. Once an extension reaction is completed, the first and second probes bound to target nucleic acids are dissociated by heating the reaction mixture above the melting temperature of the hybrids. The reaction mixture is then cooled below the melting temperature of the hybrids and additional primer is permitted to associate with target nucleic acids for another round of extension reactions. After completion of all cycles, extension products are isolated and analyzed. Alternatively, chain-terminating methods other than dideoxy nucleotides may be used. For example, chain termination occurs when no additional bases are available for incorporation at the next available nucleotide on the primer.

A particularly powerful means of analyzing genetic information from DNA amplified using the disclosed methods is DNA chip technology. DNA chips and microarrays comprising arrays of oligonucleotide or polynucleotide probes can be used to determine whether a target nucleic acid has a nucleotide sequence identical to or different from a specific reference sequence. The basic chip or microarray encompasses an array of oligonucleotide or polynucleotide probes immobilized on a solid support. Chips for screening and detection are designed to contain probes exhibiting complementarity to one or more selected sequences whose sequence is known. Chips are used to read a target sequence comprising either the reference sequence itself or variants of that sequence. Target sequences may differ from the reference sequence at one or more positions but show a high overall degree of sequence identity with the reference sequence (e.g., at least 75, 90, 95, 99, 99.9, or 99.99%). Hybridization of a target sequence to an immobilized probe results in a detectable signal. Signal can be delivered for example by conformational changes occurring in the probe, quenching or excitation of a label incorporated into the bound probe, or by quenching or excitation of a label incorporated into the target. Signal delivery may be read manually, mechanically, or digitally. A number of patents, herein incorporated by reference, disclose the preparation and use of DNA chips and microarrays including: U.S. Pat. Nos. 5,837,832, 6,156,501, 6,174,683, and 5,985,567. Additionally, allele specific primer extension can be combined with primer arrays for high-throughput genotyping of SNPs (see Pastinen et al., *Genome Res* 10(7):1031–42, 2000, incorporated herein by reference).

In the context of the present disclosure, it is specifically contemplated that the DNA amplification products of the disclosed methods may be analyzed using DNA chips or microarrays in order to detect specific genetic sequences, including genetic polymorphisms or mutations, such as for example SNPs. In one embodiment, it is envisioned that genomic DNA will be amplified utilizing the methods of the present disclosure in order to produce a library of DNA sequences theoretically encompassing the entire genomic sequence. The amplified DNA products may then be passed over a DNA chip or microarray encompassing oligonucleotide or polynucleotide probes. The ability or inability of the amplified DNA to hybridize to the microarray or DNA chip will facilitate the characterization of the specific sequences and their polymorphisms present in the DNA sample.

One embodiment of the present disclosure involves fluorescence in situ hybridization (FISH) analysis of chromosomes. First, a chromosomal DNA sample of interest is obtained. This sample may be a YAC chromosomal insert, a sample of microdissected chromosome, a cosmid DNA insert, a PAC DNA insert, a plasmid insert, or a phage insert, for example lambda phage. For example, YAC DNA may be isolated from the other yeast chromosomes on a pulsed field electrophoresis gel. Once obtained, the DNA is amplified by the disclosed method. The amplified DNA can then be labeled by a further PCR that contains a labeled nucleotide base which will be incorporated into the amplified product. Using PCR to label DNA is well known to those of skill in the art. The label may include, but is not limited to, biotin, Spectrum-Orange, or Spectrum-Green. Using the disclosed method for amplifying DNA, no prior purification of the DNA is required, and the method results in a substantial improvement in the speed of probe preparation and in the quality of the FISH signal over other DNA amplification strategies. The ability to obtain such reliable FISH signals will allow new ways of screening for the presence of common translocations in a variety of human tumors.

Additionally, labeled amplified DNA can be hybridized to a chromosome preparation such as interphase or, preferably, metaphase spreads. In metaphase spreads, the chromosomes are shortened and thickened and are more easily visualized and identified. Hybridization with the labeled probe allows one to determine the particular chromosome and the position on the chromosome from which the amplified probe was derived. Amplified, labeled DNA may also be hybridized to interphase nuclei in order to determine the number of hybridization sites in the nucleus. The hybridized probes that are labeled with biotin can be visualized with fluorescein-isothiocyanate conjugated avidin under a fluorescence microscope. Probes labeled with Spectrum-Orange or Spectrum-Green are directly visualized by fluorescence microscopy.

The methods and preferred embodiments of the present disclosure have been described above. Many techniques and methods are well known to those of skill in the art and may be used to assist practitioners in carrying out the methods of the present disclosure. The following is a general description of some of these techniques.

Nucleic Acids:

Genes are sequences of DNA in an organism's genome encoding information that is converted into various products making up a whole cell. They are expressed by the process of transcription, which involves copying the sequence of DNA into RNA. Most genes encode information to make proteins, but some encode RNAs involved in other processes. If a gene encodes a protein, its transcription product is called mRNA ("messenger" RNA). After transcription in the nucleus (where DNA is located), the mRNA is transported into the cytoplasm for the process of translation, which converts the code of the mRNA into a sequence of amino acids to form protein. In order to direct transport of mRNA into the cytoplasm, the 3' ends of mRNA molecules are post-transcriptionally modified by the addition of several adenylate residues to form the "polyA" tail. This characteristic modification distinguishes gene expression products destined to make protein from other molecules in the cell, and thereby provides one means for detecting and monitoring the gene expression activities of a cell.

1. Oligonucleotide Probes and Primers

Nucleic acid sequences that are "complementary" are those that are capable of base-pairing according to the standard Watson-Crick complementary rules. That is, the larger purines will base pair with the smaller pyrimidines to form combinations of guanine paired with cytosine (G:C) and adenine paired with either thymine (A:T) in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing. As used herein, the term "complementary" sequences means nucleic acid sequences that are substantially complementary, as may be assessed by the same nucleotide comparison set forth above, or as defined as being capable of annealing to the nucleic acid segment being described under relatively stringent conditions such as those described herein.

The term primer, as defined herein, is meant to encompass any nucleic acid that is capable of priming the synthesis of a nascent nucleic acid in a template-dependent process. Sequence specific primers should be of sufficient length to provide specific annealing to the targeted RNA or DNA sequence. The use of a primer of between about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 75, 80, 85, 90, 95, and 100 or more nucleotides in length allows the formation of a duplex molecule that is both stable and selective, although shorter and longer primers are specifically contemplated in the context of the present disclosure. For initial DNA amplification steps, hybridization of as few as 5 to 9 nucleotide bases is contemplated. Complementary sequences over stretches greater than 20 bases in length are generally preferred for subsequent amplification steps, in order to increase stability and selectivity of the hybrid, and thereby improve the quality and degree of particular hybrid molecules obtained.

Although shorter primers are easier to make and increase in vivo accessibility, numerous other factors are involved in determining the specificity of hybridization. Both binding affinity and sequence specificity of a primer to its complementary target increases with increasing length. It is contemplated that exemplary primers of 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 75, 80, 85, 90, 95, and 100 or more nucleotide base pairs will be used, although others are contemplated as well. Accordingly, nucleotide sequences may be selected for their ability to selectively form duplex molecules with complementary stretches of genes, DNA, or RNAs, or more specifically to provide primers for amplification of DNA or RNA preparations including DNA or RNA directly or indirectly derived from cells, cell lysates, and tissues. Probes and primers of the present disclosure are used to amplify DNA, as well as detect genes, changes in gene expression, gene polymorphisms, single nucleotide polymorphisms, and changes in mRNA expression where one could be detecting virtually any gene or genes of interest from any species. The target polynucleotide will be RNA molecules, mRNA, cDNA, DNA, or amplified DNA. By varying the stringency of annealing, and the region of the primer, different targets may be discovered.

Primers may be chemically synthesized by methods well known within the art. Chemical synthesis methods allow for the placement of detectable labels such as fluorescent labels, radioactive labels, etc. to be placed virtually anywhere within the polynucleic acid sequence. Solid phase methods as well as other methods of oligonucleotide or polynucleotide synthesis known to one of ordinary skill may used within the context of the disclosure.

It is specifically contemplated that a wide variety of appropriate detection or recognition means are known in the art and may be incorporated into the primers. Such labels may include, but are not limited to: fluorescent labels, radioactive labels, mass labels, affinity labels, chromophores, dyes, electroluminescence, chemiluminescence, enzymatic tags, or other ligands, such as avidin/biotin, or antibodies, which are capable of being detected and are described below.

2. DNA Amplification

One of the best known amplification methods is PCR™, which is described in detail in U.S. Pat. Nos. 4,683,195, 4,683,202 and 4,800,159, each incorporated herein by reference. While PCR™ is considered to be an acceptable means of carrying out DNA amplification, it is specifically contemplated that the methods of the present disclosure may be carried out using alternate amplification techniques which would be well known to one of ordinary skill and are briefly discussed below. In PCRTM, pairs of primers that selectively hybridize to nucleic acids are used under conditions that permit selective hybridization. The term primer, as used herein, encompasses any nucleic acid that is capable of priming the synthesis of a nascent nucleic acid in a template-dependent process. Primers may be provided in double-stranded or single-stranded form, although the single-stranded form is preferred. The primers are used in any one of a number of template dependent processes to amplify the target-gene sequences present in a given template sample.

The nucleic acid target for the disclosed DNA amplification method is generally considered to be any nucleic acid or nucleic acid analog capable of being amplified by techniques well known in the art. By way of example, target nucleic acids specifically contemplated in the context of the disclosure, may include, but is not limited to: genomic DNA, cDNA, RNA, mRNA, cosmid DNA, BAC DNA, PAC DNA, YAC DNA, and synthetic DNA. In a contemplated embodiment, genomic DNA is from a prokaryotic or eukaryotic cell or tissue and utilized as the sample DNA in the disclosed DNA amplification method. In other embodiments, poly-A mRNA is isolated and reverse transcribed (referred to as RT) to obtain cDNA, which is then used as the sample DNA for DNA amplification using the presently disclosed method. In other contemplated embodiments, cDNA may be obtained and used as the sample DNA to be amplified. In still another embodiment, RNA or mRNA is directly amplified using the disclosed DNA amplification method, wherein the starting material is an RNA sample rather than a DNA sample.

i. PCR™

In PCR™ two primer sequences are prepared which are complementary to regions on opposite complementary strands of the target-gene(s) sequence. The primers will hybridize to form a DNA:primer hybrid if the target-gene(s) sequence is present in a sample. An excess of deoxyribonucleoside triphosphates are added to a reaction mixture along with a DNA polymerase, e.g., Taq polymerase, that facilitates template-dependent nucleic acid synthesis.

If the DNA:primer hybrid is formed, the polymerase will cause the primers to be extended along the target-gene(s) sequence by adding on nucleotides. By raising and lowering the temperature of the reaction mixture, the extended primers will dissociate from the target-gene(s) to form reaction products, excess primers will bind to the target-gene(s) and to the reaction products and the process is repeated. These multiple rounds of amplification, referred to as "cycles," are conducted until a sufficient amount of amplification product is produced.

Next, the amplification product is detected. In certain applications, the detection may be performed by visual means. Alternatively, the detection may involve indirect identification of the product via fluorescent labels, chemiluminescence, radioactive scintigraphy of incorporated radiolabel or incorporation of labeled nucleotides, mass labels or even via a system using electrical or thermal impulse signals.

ii LCR

Another method for amplification is the ligase chain reaction ("LCR"), disclosed in European Patent Application No. 320,308, incorporated herein by reference. In LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR™, bound ligated units dissociate from the target and then serve as "target sequences" for ligation of excess probe pairs. U.S. Pat. No. 4,883,750, incorporated herein by reference, describes a method similar to LCR for binding probe pairs to a target sequence.

iii. Qbeta Replicase

Qbeta Replicase, described in PCT Patent Application No. PCT/US87/00880, also may be used as still another amplification method in the present disclosure. In this method, a replicative sequence of RNA which has a region complementary to that of a target is added to a sample in the presence of an RNA polymerase. The polymerase will copy the replicative sequence which can then be detected.

iv. Isothermal Amplification

An isothermal amplification method, in which restriction endonucleases and ligases are used to achieve the amplification of target molecules that contain nucleotide 5'-[α-thio]-triphosphates in one stand of a restriction site also may be useful in the DNA amplification. Such an amplification method is described by Walker et al. (*Nucleic Acids Res* 20(7):1691–6, 1992), incorporated herein by reference.

v. Strand Displacement Amplification

Strand Displacement Amplification (SDA) is another method of carrying out isothermal amplification of nucleic acids which involves multiple rounds of strand displacement and synthesis, i.e., nick translation. The SDA technique is described in U.S. Pat. Nos. 5,712,124, 5,648,211 and 5,455,166, herein incorporated by reference. A similar method, called Repair Chain Reaction (RCR), involves annealing several probes throughout a region targeted for amplification, followed by a repair reaction in which only two of the four bases are present. The other two bases can be added as biotinylated derivatives for easy detection. A similar approach is used in SDA.

vi. Cyclic Probe Reaction

Target specific sequences can also be detected using a cyclic probe reaction (CPR). In CPR, a probe having 3' and 5' sequences of non-specific DNA and a middle sequence of specific RNA is hybridized to DNA that is present in a sample. Upon hybridization, the reaction is treated with RNase H, and the products of the probe identified as distinctive products are released after digestion. The original template is annealed to another cycling probe and the reaction is repeated.

vii. Transcription-Based Amplification

Other nucleic acid amplification procedures specifically contemplated in the context of the present disclosure include transcription-based amplification systems (rAS), including nucleic acid sequence based amplification (NASBA) and 3SR, Kwoh et al., *Proc Natl Acad Sci USA*, 86:1173–77, 1989; PCT Patent Application WO 88/10315 et al., 1989 (each incorporated herein by reference).

In NASBA, the nucleic acids can be prepared for amplification by standard phenol/chloroform extraction, heat denaturation of a clinical sample, treatment with lysis buffer, and minispin columns for isolation of DNA and RNA or guanidinium chloride extraction of RNA. These amplification techniques involve annealing a primer which has target specific sequences. Following polymerization, DNA/RNA hybrids are digested with RNase H while double stranded DNA molecules are heat denatured again. In either case the single stranded DNA is made fully double stranded by addition of second target specific primer, followed by polymerization. The double-stranded DNA molecules are then multiply transcribed by a polymerase such as T7 or SP6. In an isothermal cyclic reaction, the RNAs are reverse transcribed into double stranded DNA, and transcribed once again with a polymerase such as T7 or SP6. The resulting products, whether truncated or complete, indicate target specific sequences.

viii. Other Amplification Methods

Other amplification methods, as described in British Patent Application No. GB 2,202,328, and in PCT Patent Application No. PCT/US89/01025, each incorporated herein by reference, may be used in accordance with the present disclosure. In the former application, "modified" primers are used in a PCR™-like template and enzyme dependent synthesis. The primers may be modified by labeling with a capture moiety (e.g., biotin) and/or a detector moiety (e.g., enzyme). In the latter application, an excess of labeled probes are added to a sample. In the presence of the target sequence, the probe binds and is cleaved catalytically. After cleavage, the target sequence is released intact to be bound by excess probe. Cleavage of the labeled probe signals the presence of the target sequence.

Davey et al., European Patent Application No. 329,822 (incorporated herein by reference) disclose a nucleic acid amplification process involving cyclically synthesizing single-stranded RNA ("ssRNA"), ssDNA, and double-stranded DNA (dsDNA), which may be used in accordance with the present disclosure. The ssRNA is a first template for a first primer oligonucleotide, which is elongated by reverse transcriptase (RNA-dependent DNA polymerase). The RNA is then removed from the resulting DNA:RNA duplex by the action of ribonuclease H (RNase H, an RNase specific for RNA in duplex with either DNA or RNA). The resultant ssDNA is a second template for a second primer, which also includes the sequences of an RNA polymerase promoter (exemplified by T7 RNA polymerase) 5' of its homology to the template. This primer is then extended by DNA polymerase (exemplified by the large "Klenow" fragment of *E.coli* DNA polymerase 1), resulting in a double-stranded DNA molecule, having a sequence identical to that of the original RNA between the primers and having additionally, at one end, a promoter sequence. This promoter sequence can be used by the appropriate RNA polymerase to make many RNA copies of the DNA. These copies can then reenter the cycle leading to very swift amplification. With proper choice of enzymes, this amplification can be done isothermally without adding enzymes at each cycle. Because of the cyclical nature of this process, the starting nucleic acid sequence can be either DNA or RNA.

Miller et al., PCT Patent Application WO 89/06700 (incorporated herein by reference), disclose a nucleic acid sequence amplification scheme based on the hybridization of a promoter/primer sequence to a target single-stranded DNA followed by transcription of many RNA copies of the sequence. This scheme is not cyclic, i.e., new templates are not produced from the resultant RNA transcripts.

Other suitable amplification methods include "race and "one-sided PCR™" (Frohman, In: PCR Protocols: A Guide To Methods And Applications, Academic Press, N.Y., 1990, each herein incorporated by reference). Methods based on ligation of two (or more) oligonucleotides in the presence of nucleic acid having the sequence of the resulting "di-oligonucleotide," thereby amplifying the di-oligonucleotide, also may be used to amplify DNA in accordance with the present disclosure (Wu et al., *Genomics* 4:560–569, 1989, incorporated herein by reference).

3. Restriction Enzymes

Restriction enzymes recognize specific short DNA sequences four to eight nucleotides long (see Table 1), and cleave DNA at a site within this sequence. In the context of the present disclosure, restriction enzymes may be used to cleave DNA molecules at sites corresponding to various restriction-enzyme recognition sites prior to or subsequent to the amplification reaction.

Since the sequence of the recognition site for a variety of restriction enzymes is well known in the art (e.g., see Table 1 below), primers can be designed that contain nucleotides corresponding to the recognition sequences. Primer sets can have in addition to the restriction recognition sequence degenerate sequences corresponding to different combinations of nucleotide sequences. Table 1 below exemplifies restriction enzymes and their cleavage sites that may be useful in the present disclosure.

TABLE 1

RESTRICTION ENZYMES

| Enzyme Name | Recognition Sequence |
| --- | --- |
| AatII | GACGTC |
| Acc65 I | GGTACC |
| Acc I | GTMKAC |
| Aci I | CCGC |
| Acl I | AACGTT |
| Afe I | AGCGCT |
| Afl II | CTTAAC |
| Afl III | ACRYCT |
| Age I | ACCGGT |
| Ahd I | GACNNNNNGTC |
| Alu I | AGCT |
| Alw I | GGATC |
| AlwN I | CAGNNNCTG |
| Apa I | GGGCCC |
| ApaL I | GTGCAC |
| Apo I | RAATTY |
| Asc I | GGCGCGCC |
| Ase I | ATTAAT |
| Ava I | CYCGRG |
| Ava II | GGWCC |
| Avr II | CCTAGG |
| Bae I | NACNNNNGTAPyCN |
| BamH I | GGATCC |
| Ban I | GGYRCC |
| Ban II | GRGCYC |
| Bbs I | GAAGAC |
| Bbv I | GCAGC |
| BbvC I | CCTCAGC |
| Bcg I | CGANNNNNNTGC |
| BciV I | GTATCC |
| Bcl I | TGATCA |
| Bfa I | CTAG |
| Bgl I | GCCNNNNNGGC |
| Bgl II | AGATCT |
| Blp I | GCTNAGC |
| Bmr I | ACTGGG |
| Bpm I | CTGGAG |
| BsaA I | YACGTR |
| BsaB I | GATNNNNATC |

TABLE 1-continued

RESTRICTION ENZYMES

| Enzyme Name | Recognition Sequence |
| --- | --- |
| BsaH I | GRCGYC |
| Bsa I | GGTCTC |
| BsaJ I | CCNNGG |
| BsaW I | WCCGGW |
| BseR I | GAGGAG |
| Bsg I | GTGCAG |
| BsiE I | CGRYCG |
| BsiHKA I | GWGCWC |
| BsiW I | CGTACG |
| Bsl I | CCNNNNNNNGG |
| BsmA I | GTCTC |
| BsmB I | CGTCTC |
| BsmF I | GGGAC |
| Bsm I | GAATGC |
| BsoB I | CYCGRG |
| Bsp1286 I | GDGCHC |
| BspD I | ATCGAT |
| BspE I | TCCGGA |
| BspH I | TCATGA |
| BspM I | ACCTGC |
| BsrB I | CCGCTC |
| BsrD I | GCAATG |
| BsrF I | RCCGGY |
| BsrG I | TGTACA |
| Bsr I | ACTGG |
| BssH II | GCGCGC |
| BssK I | CCNGG |
| Bst4C I | ACNGT |
| BssS I | CACGAG |
| BstAP I | GCANNNNTGC |
| BstB I | TTCGAA |
| BstE II | GGTNACC |
| BstF5 I | GGATGNN |
| BstN I | CCWGG |
| BstU I | CGCG |
| BstX I | CCANNNNNNTGG |
| BstY I | RGATCY |
| BstZ17 I | GTATAC |
| Bsu36 I | CCTNAGG |
| Btg I | CCPuPyGG |
| Btr I | CACGTG |
| Cac8 I | GCNNGC |
| Cla I | ATCGAT |
| Dde I | CTNAG |
| Dpn I | GATC |
| Dpn II | GATC |
| Dra I | TTTAAA |
| Dra III | CACNNNGTG |
| Drd I | GACNNNNNNGTC |
| Eae I | YGGCCR |
| Eag I | CGGCCG |
| Ear I | CTCTTC |
| Eci I | GGCGGA |
| EcoN I | CCTNNNNNAGG |
| Eco0109 I | RGGNCCY |
| EcoR I | GAATTC |
| EcoR V | GATATC |
| Fau I | CCCGCNNNN |
| Fnu4H I | GCNGC |
| Fok I | GGATG |
| Fse I | GGCCGGCC |
| Fsp I | TGCGCA |
| Hae II | RGCGCY |
| Hae III | GGCC |
| Hga I | GACGC |
| Hha I | GCGC |
| Hinc II | GTYPAC |
| Hind III | AAGCTT |
| Hinf I | GANTC |
| HinPl I | GCGC |
| Hpa I | GTTAAC |
| Hpa II | CCGG |
| Hph I | GGTGA |
| Kas I | GGCGCC |
| Kpn I | GGTACC |

TABLE 1-continued

RESTRICTION ENZYMES

| Enzyme Name | Recognition Sequence |
| --- | --- |
| Mbo I | GATC |
| Mbo II | GAAGA |
| Mfe I | CAATTG |
| Mlu I | ACGCGT |
| Mly I | GAGTCNNNNN |
| Mnl I | CCTC |
| Msc I | TGGCCA |
| Mse I | TTAA |
| Msl I | CAYNNNNRTG |
| MspAl I | CMGCKG |
| Msp I | CCGG |
| Mwo I | GCNNNNNNNGC |
| Nae I | GCCGGC |
| Nar I | GGCGCC |
| Nci I | CCSGG |
| Nco I | CCATGG |
| Nde I | CATATG |
| NgoMI V | GCCGGC |
| Nhe T | GCTAGC |
| Nla III | CATG |
| Nla IV | GGNNCC |
| Not I | GCGGCCGC |
| Nru I | TCGCGA |
| Nsi I | ATGCAT |
| Nsp I | RCATGY |
| Pac I | TTAATTAA |
| PaeR7 I | CTCGAG |
| Pci I | ACATGT |
| PflF I | GACNNNGTC |
| PflM I | CCANNNNNTGG |
| Ple I | GAGTC |
| Pme I | GTTTAAAC |
| Pml I | CACGTG |
| PpuM I | RGGWCCY |
| PshA I | GACNNNNGTC |
| Psi I | TTATAA |
| PspG I | CCWGG |
| PspOM I | GGGCCC |
| Pst I | CTGCAG |
| Pvu I | CGATCG |
| Pvu II | CAGCTG |
| Rsa I | GTAC |
| Rsr II | CGGWCCG |
| Sac I | GAGCTC |
| Sac II | CCGCGG |
| Sal I | GTCGAC |
| Sap I | GCTCTTC |
| Sau3A I | GATC |
| Sau96 I | GGNCC |
| Sbf I | CCTGCAGG |
| Sca I | AGTACT |
| ScrF I | CCNGG |
| SexA I | ACCWGGT |
| SfaN I | GCATC |
| Sfc I | CTRYAG |
| Sfi I | GGCCNNNNNGGCC |
| Sfo I | GGCGCC |
| SgrA I | CRCCGGYG |
| Sma I | CCCGGG |
| Sml I | CTYRAG |
| SnaB I | TACGTA |
| Spe I | ACTAGT |
| Sph I | GCATGC |
| Ssp I | AATATT |
| Stu I | AGGCCT |
| Sty I | CCWWGG |
| Swa I | ATTTAAAT |
| Taq I | TCGA |
| Tfi I | GAWTC |
| Tli I | CTCGAG |
| Tse I | GCWGC |
| Tsp45 I | GTSAC |
| Tsp509 I | AATT |
| TSpR I | CAGTG |
| Tthlll I | GACNNNGTC |

TABLE 1-continued

RESTRICTION ENZYMES

| Enzyme Name | Recognition Sequence |
| --- | --- |
| Xba I | TCTAGA |
| Xcm I | CCANNNNNNNNNTGG |
| Xho I | CTCGAG |
| Xma I | CCCGGG |
| Xmn I | GAANNNNTTC |

4. Other Enzymes

A polymerase is an enzyme that catalyses the synthesis of nucleic acids on preexisting nucleic acid templates, assembling RNA from ribonucleotides or DNA from deoxyribonucleotides. Polymerases specifically contemplated in the context of the present disclosure may be naturally isolated, modified, or synthetic. While it is generally contemplated that the polymerase employed will be thermostable, non-thermostable polymerases may also be employed in the context of the present disclosure. Tables 2 and 3 set forth exemplary polymerases and nucleic acid modifying enzymes that may be used in the context of the disclosure.

TABLE 2

POLYMERASES

Thermostable DNA Polymerases:

OmniBase ™ Sequencing Enzyme
Pfu DNA Polymerase
Taq DNA Polymerase
Taq DNA Polymerase, Sequencing Grade
TaqBead ™ Hot Start Polymerase
AmpliTaq Gold
Vent DNA Polymerase
Tub DNA Polymerase
TaqPlus DNA Polymerase
Tfl DNA Polymerase
Tli DNA Polymerase
Tth DNA Polymerase DNA Polymerases:

DNA Polymerase I, Klenow Fragment, Exonuclease Minus
DNA Polymerase I
DNA Polymerase I Large (Klenow) Fragment
Terminal Deoxynucleotidyl Transferase
T7 DNA Polymerase
T4 DNA Polymerase

REVERSE TRANSCRIPTASES

AMV Reverse Transcriptase
M-MLV Reverse Transcriptase

TABLE 3

DNA/RNA MODIFYING ENZYMES

Ligases:

T4 DNA Ligase

Kinases:

T4 Polynucleotide Kinase

5. Labels

Recognition moieties incorporated into primers, incorporated into the amplified product during amplification, or attached to probes are useful in identification of the amplified molecules. A number of different labels may be used for this purpose such as, for example: fluorophores, chromophores, radio-isotopes, enzymatic tags, antibodies, chemiluminescence, electroluminescence, affinity labels, etc. One of skill in the art will recognize that these and other fluorophores not mentioned herein can also be used with success in this disclosure.

Examples of affinity labels include but are not limited to the following: an antibody, an antibody fragment, a receptor protein, a hormone, biotin, DNP, or any polypeptide/protein molecule that binds to an affinity label and may be used for separation of the amplified gene.

Examples of enzyme tags include enzymes such as urease, alkaline phosphatase, or peroxidase. Additionally, colorimetric indicator substrates can be employed to provide a detection means visible to the human eye or spectrophotometrically, to identify specific hybridization with complementary nucleic acid-containing samples. All these examples are generally known in the art and the skilled artisan will recognize that the present disclosure is not limited to the examples described above.

The following fluorophores are specifically contemplated to be useful in the present disclosure: Alexa 350, Alexa 430, AMCA, BODIPY 630/650, BODIPY 650/665, BODIPY-FL, BODIPY-R6G, BODIPY-TMR, BODIPY-TRX, Cascade Blue, Cy2, Cy3, Cy5, 6-FAM, Fluorescein, HEX, 6-JOE, Oregon Green 488, Oregon Green 500, Oregon Green 514, Pacific Blue, REG, Rhodamine Green, Rhodamine Red, ROX, TAMRA, TET, Tetramethylrhodamine, and Texas Red.

6. Separation and Quantitation Methods

Following amplification, it may be desirable to separate the amplification products of several different lengths from each other, from the template, and from excess primers for the purpose of analysis or more specifically for determining whether specific amplification has occurred.

i. Gel Electrophoresis

In one embodiment, amplification products are separated by agarose, agarose-acrylamide or polyacrylamide gel electrophoresis using standard methods (Sambrook et al., "Molecular Cloning," *A Laboratory Manual*, 2d Ed., Cold Spring Harbor Laboratory Press, New York, 13.7–13.9:1989). Gel electrophoresis techniques are well known in the art.

ii. Chromatographic Techniques

Alternatively, chromatographic techniques may be employed to effect separation. There are many kinds of chromatography which may be used in the present disclosure: adsorption, partition, ion-exchange, and molecular sieve, as well as many specialized techniques for using them including column, paper, thin-layer and gas chromatography (Freifelder, Physical Biochemstry Applications to Biochemistry and Molecular Biology, 2nd ed. Wm. Freeman and Co., New York, N.Y., 1982). Yet another alternative is to capture nucleic acid products labeled with, for example, biotin or antigen with beads bearing avidin or antibody, respectively.

iii. Microfluidic Techniques

Microfluidic techniques include separation on a platform such as microcapillaries, including by way of example those designed by ACLARA BioSciences Inc., or the LabChip™ by Caliper Technologies Inc. These microfluidic platforms require only nanoliter volumes of sample, in contrast to the microliter volumes required by other separation technologies. Miniaturizing some of the processes involved in genetic analysis has been achieved using microfluidic devices. For example, published PCT Application No. WO 94/05414, to Northrup and White, incorporated herein by reference, reports an integrated micro-PCR™ apparatus for collection and amplification of nucleic acids from a specimen. U.S. Pat. Nos. 5,304,487, 5,296,375, and 5,856,174 describe apparatus and methods incorporating the various processing and analytical operations involved in nucleic acid analysis and are incorporated herein by reference.

iv. Capillary Electrophoresis

In some embodiments, it may be desirable to provide an additional, or alternative means for analyzing the amplified DNA. In these embodiments, microcapillary arrays are contemplated to be used for the analysis. Microcapillary array electrophoresis generally involves the use of a thin capillary or channel that may or may not be filled with a particular separation medium. Electrophoresis of a sample through the capillary provides a size based separation profile for the sample. Microcapillary array electrophoresis generally provides a rapid method for size-based sequencing, PCR™ product analysis, and restriction fragment sizing. The high surface to volume ratio of these capillaries allows for the application of higher electric fields across the capillary without substantial thermal variation across the capillary, consequently allowing for more rapid separations. Furthermore, when combined with confocal imaging methods, these methods provide sensitivity in the range of attomoles, which is comparable to the sensitivity of radioactive sequencing methods. Microfabrication of microfluidic devices including microcapillary electrophoretic devices has been discussed in detail in, for example, Jacobson et al., *Anal Chem*, 66:1107–1113, 1994; Effenhauser et al., *Anal Chem*, 66:2949–2953, 1994; Harrison et al., *Science*, 261:895–897, 1993; Effenhauser et al., *Anal Chem*, 65:2637–2642, 1993; Manz et al., *J. Chromatogr* 593:253–258, 1992; and U.S. Pat. No. 5,904,824, incorporated herein by reference. Typically, these methods comprise photolithographic etching of micron scale channels on a silica, silicon, or other crystalline substrate or chip, and can be readily adapted for use in the present disclosure.

Tsuda et al. (*Anal Chem*, 62:2149–2152, 1990) describes rectangular capillaries, an alternative to the cylindrical capillary glass tubes. Some advantages of these systems are their efficient heat dissipation due to the large height-to-width ratio and, hence, their high surface-to-volume ratio and their high detection sensitivity for optical on-column detection modes. These flat separation channels have the ability to perform two-dimensional separations, with one force being applied across the separation channel, and with the sample zones detected by the use of a multi-channel array detector.

In many capillary electrophoresis methods, the capillaries, e.g., fused silica capillaries or channels etched, machined, or molded into planar substrates, are filled with an appropriate separation/sieving matrix. Typically, a variety of sieving matrices known in the art may be used in the microcapillary arrays. Examples of such matrices include, e.g., hydroxyethyl cellulose, polyacrylamide, agarose, and the like. Generally, the specific gel matrix, running buffers, and running conditions are selected to maximize the separation characteristics of the particular application, e.g., the size of the nucleic acid fragments, the required resolution, and the presence of native or undenatured nucleic acid molecules. For example, running buffers may include denaturants, chaotropic agents such as urea to denature nucleic acids in the sample.

v. Mass Spectroscopy

Mass spectrometry provides a means of "weighing" individual molecules by ionizing the molecules in vacuo and making them "fly" by volatilization. Under the influence of combinations of electric and magnetic fields, the ions follow trajectories depending on their individual mass (m) and charge (z). For low molecular weight molecules, mass spectrometry has been part of the routine physical-organic repertoire for analysis and characterization of organic molecules by the determination of the mass of the parent molecular ion. In addition, by arranging collisions of this parent molecular ion with other particles (e.g., argon atoms), the molecular ion is fragmented forming secondary ions by the so-called collision induced dissociation (CID). The fragmentation pattern/pathway very often allows the derivation of detailed structural information. Other applications of mass spectrometric methods in the art are summarized in Methods in Enzymology, Vol. 193: "Mass Spectrometry" (J. A. McCloskey, editor), 1990, Academic Press, New York.

Due to the apparent analytical advantages of mass spectrometry in providing high detection sensitivity, accuracy of mass measurements, detailed structural information by CID in conjunction with an MS/MS configuration and speed, as well as on-line data transfer to a computer, there has been considerable interest in the use of mass spectrometry for the structural analysis of nucleic acids. Reviews summarizing this field include (Schram, *Methods Biochem Anal*, 34:203–287,1990) and (Crain, *Mass Spectrometry Reviews*, 9:505–554, 1990), here incorporated herein by reference. The biggest hurdle to applying mass spectrometry to nucleic acids is the difficulty of volatilizing these very polar biopolymers. Therefore, "sequencing" had been limited to low molecular weight synthetic oligonucleotides by determining the mass of the parent molecular ion and through this, confirming the already known sequence, or alternatively, confirming the known sequence through the generation of secondary ions (fragment ions) via CID in an MS/MS configuration utilizing, in particular, for the ionization and volatilization, the method of fast atomic bombardment (FAB mass spectrometry) or plasma desorption (PD mass spectrometry). As an example, the application of FAB to the analysis of protected dimeric blocks for chemical synthesis of oligodeoxynucleotides has been described (Koster et al., *Biomedical Environmental Mass Spectrometry* 14:111–116, 1987).

Two ionization/desorption techniques are electrospray/ionspray (ES) and matrix-assisted laser desorption/ionization (MALDI). ES mass spectrometry was introduced by Fenn et al., *J. Phys. Chem,. 88;4451–59,1984*; PCT Application No. WO 90/14148 and its applications are summarized in review articles, for example, Smith et al., *Anal Chem* 62:882–89, 1990, and Ardrey, *Electrospray Mass Spectrometry, Spectroscopy Europe, 4:10–18, 1992*. As a mass analyzer, a quadrupole is most frequently used. The determination of molecular weights in femtomole amounts of sample is very accurate due to the presence of multiple ion peaks that can be used for the mass calculation.

MALDI mass spectrometry, in contrast, can be particularly attractive when a time-of-flight (TOF) configuration is used as a mass analyzer. The MALDI-TOF mass spectrometry was introduced by (Hillenkamp et al., Biological Mass Spectrometry eds. Burlingame and McCloskey, Elsevier Science Publishers, Amsterdam, pp. 49–60, 1990). Since, in most cases, no multiple molecular ion peaks are produced with this technique, the mass spectra, in principle, look simpler compared to ES mass spectrometry. DNA molecules up to a molecular weight of 410,000 daltons could be desorbed and volatilized (Williams et al., *Science*, 246:1585–87, 1989). More recently, the use of infrared lasers (IR) in this technique (as opposed to UV-lasers) has been shown to provide mass spectra of larger nucleic acids such as synthetic DNA, restriction enzyme fragments of plasmid DNA, and RNA transcripts up to a size of 2180 nucleotides (Berkenkamp et al., *Science*, 281:260–2, 1998). Berkenkamp also describes how DNA and RNA samples can be analyzed by limited sample purification using MALDI-TOF IR.

In Japanese Patent No. 59-131909, an instrument is described that detects nucleic acid fragments separated either by electrophoresis, liquid chromatography or high speed gel filtration. Mass spectrometric detection is achieved by incorporating into the nucleic acids atoms that normally do not occur in DNA such as S, Br, I or Ag, Au, Pt, Os, Hg.

vii. Energy Transfer

Labeling hybridization oligonucleotide probes with fluorescent labels is a well known technique in the art and is a sensitive, nonradioactive method for facilitating detection of probe hybridization. More recently developed detection methods employ the process of fluorescence energy transfer (FET) rather than direct detection of fluorescence intensity for detection of probe hybridization. FET occurs between a donor fluorophore and an acceptor dye (which may or may not be a fluorophore) when the absorption spectrum of one (the acceptor) overlaps the emission spectrum of the other (the donor) and the two dyes are in close proximity. Dyes with these properties are referred to as donor/acceptor dye pairs or energy transfer dye pairs. The excited-state energy of the donor fluorophore is transferred by a resonance dipole-induced dipole interaction to the neighboring acceptor. This results in quenching of donor fluorescence. In some cases, if the acceptor is also a fluorophore, the intensity of its fluorescence may be enhanced. The efficiency of energy transfer is highly dependent on the distance between the donor and acceptor, and equations predicting these relationships have been developed by Forster, *Ann Phys* 2:55–75, 1948. The distance between donor and acceptor dyes at which energy transfer efficiency is 50% is referred to as the Forster distance ($R_o$). Other mechanisms of fluorescence quenching are also known in the art including, for example, charge transfer and collisional quenching.

Energy transfer and other mechanisms that rely on the interaction of two dyes in close proximity to produce quenching are an attractive means for detecting or identifying nucleotide sequences, as such assays may be conducted in homogeneous formats. Homogeneous assay formats differ from conventional probe hybridization assays that rely on the detection of the fluorescence of a single fluorophore label because heterogeneous assays generally require additional steps to separate hybridized label from free label. Several formats for FET hybridization assays are reviewed in Nonisotopic DNA Probe Techniques (Academic Press, Inc., pgs. 311–352, 1992).

Homogeneous methods employing energy transfer or other mechanisms of fluorescence quenching for detection of nucleic acid amplification have also been described. Higuchi et al. (*Biotechnology* 10:413–417, 1992), discloses methods for detecting DNA amplification in real-time by monitoring increased fluorescence of ethidium bromide as it binds to double-stranded DNA. The sensitivity of this method is limited because binding of the ethidium bromide is not target specific and background amplification products are also detected. Lee et al. (*Nucleic Acids Res* 21:3761–3766, 1993), discloses a real-time detection method in which a doubly-labeled detector probe is cleaved in a target amplification-specific manner during PCR™. The detector probe is hybridized downstream of the amplification primer so that the 5'-3' exonuclease activity of Taq polymerase digests the detector probe, separating two fluorescent dyes, which then form an energy transfer pair. Fluorescence intensity increases as the probe is cleaved. Published PCT application WO 96/21144 discloses continuous fluorometric assays in which enzyme-mediated cleavage of nucleic acids results in increased fluorescence. Fluorescence energy transfer is suggested for use, but only in the context of a method employing a single fluorescent label that is quenched by hybridization to the target.

Signal primers or detector probes that hybridize to the target sequence downstream of the hybridization site of the amplification primers have been described for use in detection of nucleic acid amplification (U.S. Pat. No. 5,547,861). The signal primer is extended by the polymerase in a manner similar to extension of the amplification primers. Extension of the amplification primer displaces the extension product of the signal primer in a target amplification-dependent manner, producing a double-stranded secondary amplification product that may be detected as an indication of target amplification. The secondary amplification products generated from signal primers may be detected by means of a variety of labels and reporter groups, restriction sites in the signal primer that are cleaved to produce fragments of a characteristic size, capture groups, and structural features such as triple helices and recognition sites for double-stranded DNA binding proteins.

Many donor/acceptor dye pairs are known in the art and may be used in the present disclosure. These include but are not limited to: fluorescein isothiocyanate (FITC)/tetramethylrhodamine isothiocyanate (TALIC), FITC/Texas Red™ Molecular Probes, FITC/N-hydroxysuccmimidyl 1-pyrenebutyrate (PYB), FITC/eosin isothiocyanate (EITC), N-hydroxysuccinimidyl 1-pyrenesulfonate (PYS)/FITC, FITC/Rhodamine X, FITC/tetramethylrhodamine (TAMRA), and others. The selection of a particular donor/acceptor fluorophore pair is not critical. For energy transfer quenching mechanisms it is only necessary that the emission wavelengths of the donor fluorophore overlap the excitation wavelengths of the acceptor, i.e., there must be sufficient spectral overlap between the two dyes to allow efficient energy transfer, charge transfer, or fluorescence quenching. P-(dimethyl aminophenylazo) benzoic acid (DABCYL) is a non-fluorescent acceptor dye which effectively quenches fluorescence from an adjacent fluorophore, e.g., fluorescein or 5-(2'-aminoethyl) aminonaphthalene (EDANS). Any dye pairs that produce fluorescence quenching in the detector nucleic acids are suitable for use in the methods of the disclosure, regardless of the mechanism by which quenching occurs. Terminal and internal labeling methods are both known in the art and may be routinely used to link the donor and acceptor dyes at their respective sites in the detector nucleic acid.

viii. Microarrays and Chip Technologies

Specifically contemplated in the present disclosure is the use or analysis of amplified products by microarrays and/or chip-based DNA technologies such as those described by (Hacia et al., Nature Genet, 14:441–449, 1996) and (Shoemaker et al., Nature Genetics, 14:450–456, 1996). These techniques involve quantitative methods for analyzing large numbers of genes rapidly and accurately. By tagging genes with oligonucleotides or using fixed probe arrays, chip technology can be employed to segregate target molecules as high density arrays and screen these molecules on the basis of hybridization (Pease et al., Proc Natl Acad Sci USA, 91:5022–5026, 1994; Fodor et al, Nature, 364:555–556, 1993).

ix. OIA.

Also contemplated is the use of BioStar's OIA technology to quantitate amplified products. OIA uses the mirror-like surface of a silicon wafer as a substrate. A thin film optical coating and capture antibody is attached to the silicon wafer. White light reflected through the coating appears as a golden background color. This color does not change until the thickness of the optical molecular thin film is changed.

When a positive sample is applied to the wafer, binding occurs between the ligand and the antibody. When substrate is added to complete the mass enhancement, a corresponding change in color from gold to purple/blue results from the increased thickness in the molecular thin film. The technique is described in U.S. Pat. No. 5,541,057, herein incorporated by reference.

x. Real Time PCR

Amplified RNA or DNA may be quantitated using the Real-Time PCR technique (Higuchi et al., Biotechnology 10:413–417, 1992). By determining the concentration of the amplified products that have completed the same number of cycles and are in their linear ranges, it is possible to determine the relative concentrations of the specific target sequence in the original DNA mixture. For example, if the DNA mixtures are cDNAs synthesized from RNAs isolated from different tissues or cells, the relative abundance of the specific mRNA from which the target sequence was derived can be determined for the respective tissues or cells. This direct proportionality between the concentration of the amplification products and the relative mRNA abundance is only true in the linear range of the amplification reaction.

The final concentration of the target DNA in the plateau portion of the curve is determined by the availability of reagents in the reaction mixture and is independent of the original concentration of target DNA. Therefore, the first condition that must be met before the relative abundance of a RNA or DNA species can be determined by Real-Time PCR for a collection of RNA or DNA populations is that the concentrations of the amplified products must be sampled when the reaction products are in the linear portion of their curves. The second condition that must be met for an RT-PCR experiment to successfully determine the relative abundance of a particular mRNA species is that relative concentrations of the amplifiable cDNAs must be normalized to some independent standard. The goal of a Real-Time PCR experiment is to determine the abundance of a particular RNA or DNA species relative to the average abundance of all RNA or DNA species in the sample.

xi. Luminex

The Luminex technology allows the quantitation of nucleic acid products immobilized on color coded microspheres. The magnitude of the biomolecular reaction is measured using a second molecule called a reporter. The reporter molecule signals the extent of the reaction by attaching to the molecules on the microspheres. As both the microspheres and the reporter molecules are color coded, digital signal processing allows the translation of signals into real-time, quantitative data for each reaction. The standard technique is described in U.S. Pat. Nos. 5,736,303 and 6,057,107, herein incorporated by reference.

8. Identification Methods

Amplification products must be visualized in order to confirm amplification of the target-gene(s) sequences. One typical visualization method involves staining of a gel with a flourescent dye, such as ethidium bromide or Vistra Green, and visualization under UV light. Alternatively, if the amplification products are integrally labeled with radio- or fluorometrically-labeled nucleotides, the amplification products can be exposed to x-ray film or visualized under the appropriate stimulating spectra following separation.

In one embodiment, visualization is achieved indirectly, using a nucleic acid probe. Following separation of amplification products, a labeled, nucleic acid probe is brought into contact with the amplified products. The probe preferably is conjugated to a chromophore but may be radiolabeled. In another embodiment, the probe is conjugated to a binding partner, such as an antibody or biotin, where the other member of the binding pair carries a detectable moiety. In other embodiments, the probe incorporates a fluorescent dye or label. In yet other embodiments, the probe has a mass label that can be used to detect the molecule amplified. Other embodiments also contemplate the use of Taqman™ and Molecular Beacon™ probes. In still other embodiments, solid-phase capture methods combined with a standard probe may be used.

The type of label incorporated in DNA amplification products is dictated by the method used for analysis. When using capillary electrophoresis, microfluidic electrophoresis, HPLC, or LC separations, either incorporated or intercalated fluorescent dyes are used to label and detect the amplification products. Samples are detected dynamically, in that fluorescence is quantitated as a labeled species moves past the detector. If any electrophoretic method, HPLC, or LC is used for separation, products can be detected by absorption of UV light, a property inherent to DNA and therefore not requiring addition of a label. If polyacrylamide gel or slab gel electrophoresis is used, primers for the amplification reactions can be labeled with a fluorophore, a chromophore or a radioisotope, or by associated enzymatic reaction. Enzymatic detection involves binding an enzyme to a primer, e.g., via a biotin:avidin interaction, following separation of the amplification products on a gel, then detection by chemical reaction, such as chemiluminescence generated with luminol. A fluorescent signal can be monitored dynamically. Detection with a radioisotope or enzymatic reaction requires an initial separation by gel electrophoresis, followed by transfer of DNA molecules to a solid support (blot) prior to analysis. If blots are made, they can be analyzed more than once by probing, stripping the blot, and then reprobing. If amplification products are separated using a mass spectrometer no label is required because nucleic acids are detected directly.

A number of the above separation platforms can be coupled to achieve separations based on two different properties. For example, some of the PCR™ primers can be coupled with a moiety that allows affinity capture, while some primers remain unmodified. Modifications can include a sugar (for binding to a lectin column), a hydrophobic group (for binding to a reverse-phase column), biotin (for binding to a streptavidin column), or an antigen (for binding to an antibody column). Samples are run through an affinity chromatography column. The flow-through fraction is collected, and the bound fraction eluted (by chemical cleavage, salt elution, etc.). Each sample is then further fractionated based on a property, such as mass, to identify individual components.

10. Kits

The materials and reagents required for the disclosed amplification method may be assembled together in a kit. The kits of the present disclosure generally will include at least the enzymes and nucleotides necessary to carry out the claimed method along with primer sets. In a preferred embodiment, the kit will also contain directions for amplifying DNA from DNA samples.

The kits of the present disclosure also will generally include one or more preselected primer sets and/or probes that may be either specific or non-specific for genes to be amplified. Preferably, the kits will include, in a suitable container means, one or more nucleic acid probes and/or primer sets and means for detecting nucleic acids. In certain embodiments, such as in kits for use in amplification reactions, the means for detecting the nucleic acids may be a label, such as a fluorophore, a radiolabel, an enzyme tag, etc., that is linked to the nucleic acid primer or the nucleotides themselves. It is envisioned that kits may contain pairs of primer sets for each DNA amplification step of the present disclosure. It is also envisioned that kits may contain precipitation solutions to process DNA samples stored on solid mediums according to the precipitation method of the present disclosure.

Preferred kits are those suitable for use in amplifying whole genomic DNA. In a preferred kit, a first primer will preferably be provided that has a random sequence of nucleotides at its 3' end and a generic 5' of the random sequence, which hybridizes randomly to DNA. The kit will also preferably include a second primer with a generic sequence that is the same as the generic sequence of the first primer. For example, kits may be used to amplify all genes and chromosomal regions, unknown and/or known from an organisms whole genomic or chromosomal DNA. Also included in the kits may be enzymes suitable for amplifying nucleic acids, including various polymerases (RT, Taq, etc.), deoxynucleotides and buffers to provide the necessary single reaction mixture for amplification.

The kits of the present disclosure, may also contain primers with one or more of a variety of other moieties as described above.

In each case, the kits will preferably have distinct containers for each individual reagent and enzyme, as well as for each probe or primer pair. Each biological agent will generally be suitably aliquoted in their respective containers. The container means of the kits will generally include at least one vial or test tube. Flasks, bottles, and other container means into which the reagents are placed and aliquoted are also possible. The individual containers of the kit will preferably be maintained in close confinement for commercial sale. Suitable larger containers may include injection or blow-molded plastic containers into which the desired vials are retained. Instructions are preferably provided with the kit.

The following examples are included to demonstrate preferred embodiments of the present disclosure. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments that are disclosed and still obtain a like or similar result without departing from the spirit and scope of the invention.

EXAMPLE 1

The efficiency of PCR™ amplification of DNA samples stored on FTA paper processed using the presently disclosed precipitation method and the commercially produced FTA Purification Reagent (manufactured by Whatman) protocol was compared. First, four bloodstain DNA samples stored on FTA paper were processed using the disclosed precipitation method according to the following protocol: A small circle (1–3 mm) in the FTA paper sample was excised by the commercial Harris Micro-Punch manufactured by Shunderson Communication, Ottawa, Ontario, Canada, and washed with distilled water. The circle was transferred to a 96-well plate and soaked in 200 μl of DD $H_2O$ for 20 minutes. The water was changed and the circle was soaked in water again for 5 minutes. The water was next replaced with 200 μl of 0.3M NaOAc/Ethanol (50/50 v/v) solution and the paper was soaked for 5 minutes to fix the genomic DNA on the paper. The solution was removed and the paper was washed in 200 μl of 80% ethanol for 5 minutes to remove salt and to accelerate dehydration. The ethanol was removed and the paper was dried at room temperature for 15 minutes. The ethanol wash reduced the dehydration time of the FTA paper sample by at least 50%. The dehydrated paper was then used directly as the DNA for PCR amplification.

Second, the same four bloodstain DNA samples stored on FTA paper were processed according to the commercial FTA Purification Reagent manufacturer's protocol. Briefly, for each sample a small circle (1–3 mm) in the FTA paper sample was excised by the Harris Micro-Punch. The circle was transferred to a 96-well plate and soaked in 200 μl of FTA Purification Reagent for 5 minutes. The FTA reagent was changed and the wash was repeated 2 times. After the FTA Purification Reagent had been removed for the third time, 200 μl of TE buffer (10 mM Tris-HCl pH 8.0 and 0.1 mM EDTA) was added to the paper. The FTA paper was soaked in TE for 5 minutes, and then the TE solution was removed and the paper was air-dried for 1 hour. The dehydrated paper was then used directly for PCR amplification.

Both sets of dehydrated paper samples were amplified using the following conditions. The reaction mixture for each PCR contained the DNA-paper sample, 10 mM Tris HCl (pH 8.3), 5 mM $MgCl_2$, 50 mM KCl, 0.001% gelatin, 300 μM dNTP (dATP, dGTP, dCTP, and dTTP), 300 nM of the forward primer having the sequence 5'-CCTTTTCCTCTAGCATCAAGTTA-3' (SEQ ID NO:13), 300 nM of the reverse primer having the sequence 5'-CAGACTGTGTGCTTCCTACAG-3' (SEQ ID NO:14), and 1.25 unit Taq DNA polymerase, for a total volume of 50 μM. The thermocycling program for the reaction mixtures was 95° C. for 2 minutes; 15 "touchdown" cycles of 95° C. for 30 seconds, 66–51° C. for 30 seconds, and 72° C. for 30 seconds; and 35 cycles of 95° C. for 30 seconds, 50° C. for 30 seconds, and 72° C. for 30 seconds. The PCR products were subjected to electrophoresis on a 2.0% agarose gel without purification.

Figure 2:
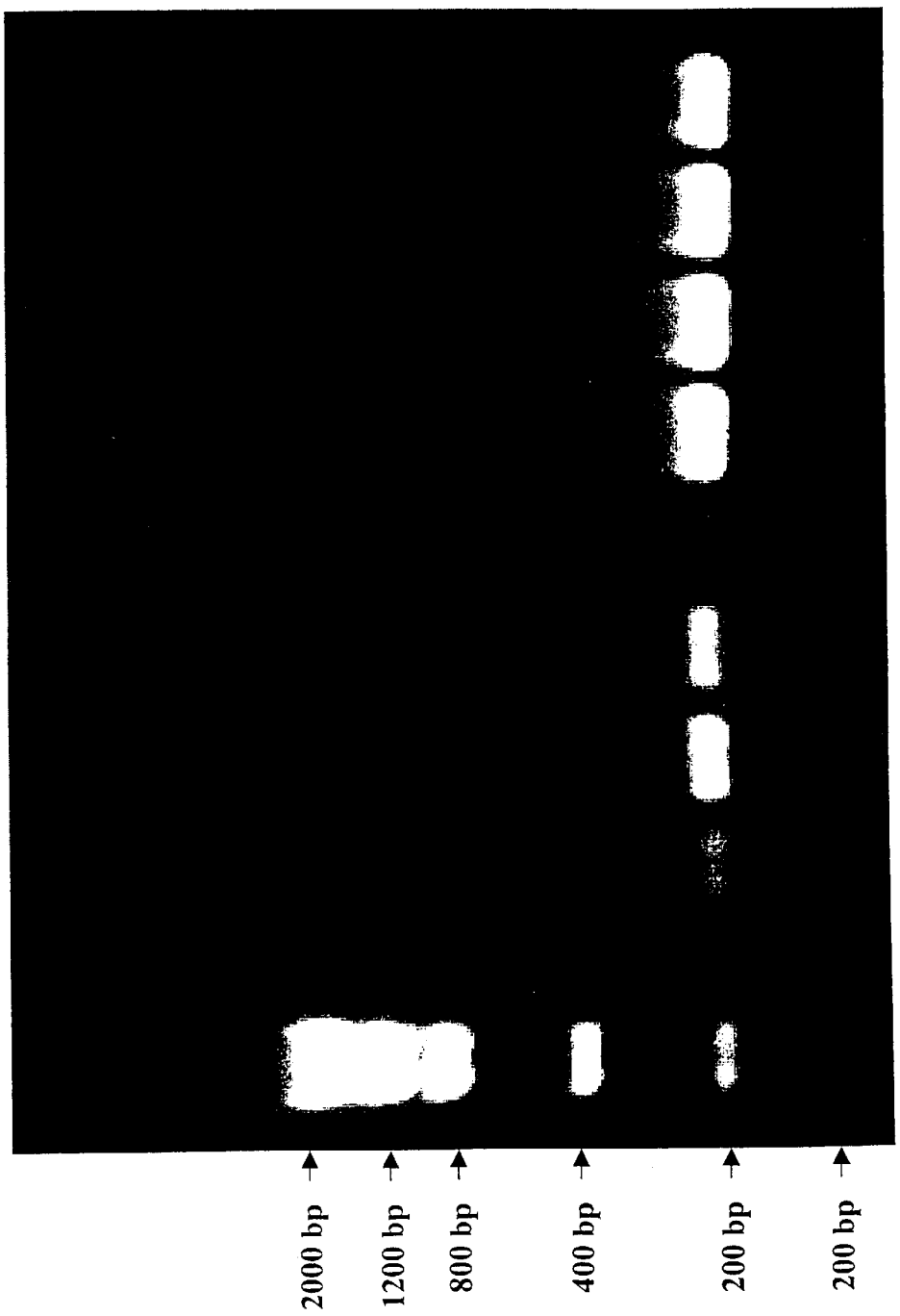
FIG. 2. PCR amplification of DNA samples (bloodstains) stored on FTA paper. The efficiency of PCR amplification of samples processed using the commercial FTA Purification Reagent is compared to samples processed using a preferred method of the present disclosure. Identical punches obtained from the same bovine bloodstains on FTA paper were treated using either the commercial FTA Purification Reagent or the precipitation method of the present disclosure. After the DNA samples were treated, the samples were subjected to PCR amplification as described in Example 1. Lane 1, DNA molecular size marker; lanes 2–5, direct PCR products of 4 bloodstain samples processed with commercial FTA Purification Reagent; lanes 7–10, direct PCR products of the identical 4 bloodstain samples as lanes 2–5, respectively, first processed with the precipitation method of the present disclosure. It is apparent that DNA samples processed using the precipitation method of the present disclosure are more consistently and optimally amplified by PCR than samples treated with FTA Purification Reagent.

FIG. 2 shows the results of direct PCR amplification of DNA samples stored on FTA paper processed using the disclosed precipitation method as compared to the FTA Purification Reagent protocol. FIG. 2. clearly demonstrates that the disclosed precipitation method greatly reduces the variation of PCR amplification efficiency found when the commercial FTA Purification Reagent is used to process DNA samples. The presently disclosed precipitation method not only offers a simpler and faster method for processing DNA samples stored on FTA paper, it also reduces the cost of processing the samples and greatly optimizes subsequent PCR amplification and genetic analysis of the DNA samples.

EXAMPLE 2

The method of amplifying whole genomic DNA of the present disclosure was used to amplify genomic DNA from bovine bloodstain samples stored on FTA paper. This method combines DNA extraction and amplification in a single operation by allowing genomic DNA in a bovine bloodstain sample to be amplified in a single reaction mixture using a single thermocycling reaction. Therefore, this method greatly reduces the risk of sample contamination and facilitates high-throughput screening. Additionally, 96-well or 384-well plates can be utilized for amplification of genomic DNA stored on FTA paper using the presently disclosed methods, which greatly facilitates a high-throughput operation. The utility and efficiency of the presently disclosed method of DNA amplification was tested by comparing PCR amplification of a known bovine SNP locus using DNA amplified by the disclosed method and DNA bound directly to FTA paper. In both experiments, the DNA samples stored on FTA paper were processed using the disclosed precipitation method as described in Example 1. Therefore, this example is designed to specifically test the efficacy of the presently disclosed method of DNA amplification for genetic analysis.

Bloodstain samples were collected and stored on FTA paper for 13 individual bovine animals. The FTA paper samples were processed using the disclosed precipitation method, and genomic DNA was amplified from one set of samples using the disclosed method of DNA amplification. Each dehydrated paper sample was amplified using the following conditions. First, the DNA sample was placed in an amplification reaction mixture that contained 10 mM Tris HCl (pH 8.3), 5 mM $MgCl_2$, 50 mM KCl, 0.001% gelatin, 300 μM dNTP (dATP, dGTP, dCTP, and dTTP), 300 nM of the first primer having the sequence of SEQ ID NO:1, 300 nM of the second primer having the sequence of SEQ ID NO:2, and 1.25 unit Taq DNA polymerase, for a total volume of about 50 μl. The entire reaction mixture was heated to 95° C. for 5 minutes to denature the sample.

Next, during the first set of reactions of DNA amplification, the reaction mixture was heated to a temperature of 95° C. for 1 minute, and cooled to a temperature of 42° C. for 5 minutes. These steps allowed the first primer to anneal with the denatured sample DNA and the Taq DNA polymerase to synthesize the complementary strand of DNA from the 3' end of the first primer. The denaturation, annealing, and extension steps were repeated again by heating the reaction mixture for 1 minute at 95° C. and then cooling the mixture to 42° C. for 5 minutes.

The second set of reactions of DNA amplification involved subsequently heating the reaction mixture to a temperature of 95° C. for 15 seconds, cooling the mixture to a temperature of 65° C. to allow the second primer to anneal to the single-stranded DNA products, and raising the mixture to a temperature of 68° C., thereby allowing the Taq DNA polymerase to synthesize the complementary strand of DNA from the 3' end of the second primer. These steps of denaturation, annealing, and extension were repeated 39 times for a total of 40 cycles.

The set of dehydrated DNA samples processed using the disclosed precipitation method only, and the set of DNA samples processed using the disclosed precipitation method, as well as amplified using the disclosed DNA amplification method, were next subjected to PCR amplification using the following conditions. The reaction mixture for each PCR contained either the dehydrated DNA-paper sample or 20 ng of amplified genomic DNA, 10 mM Tris HCl (pH 8.3), 5 mM $MgCl_2$, 50 mM KCl, 0.001% gelatin, 300 μM dNTP (dATP, dGTP, dCTP, and dTTP), 300 nM of the forward primer having the sequence 5'-CCAGCAGTTCTGAATGAAAGT-3' (SEQ ID NO:15), 300 nM of the reverse primer having the sequence 5'-ACACACAGAGGCCGTGTA-3' (SEQ ID NO:16), and 1.25 unit Taq DNA polymerase, for a total volume of 50 μl. The thermocycling program for the reaction mixtures was 95° C. for 2 minutes; 15 "touchdown" cycles of 95° C. for 30 seconds, 66–51° C. for 30 seconds, and 72° C. for 30 seconds; and 35 cycles of for 30 seconds, 50° C. for 30 seconds, and 72° C. for 30 seconds.

Figure 3:
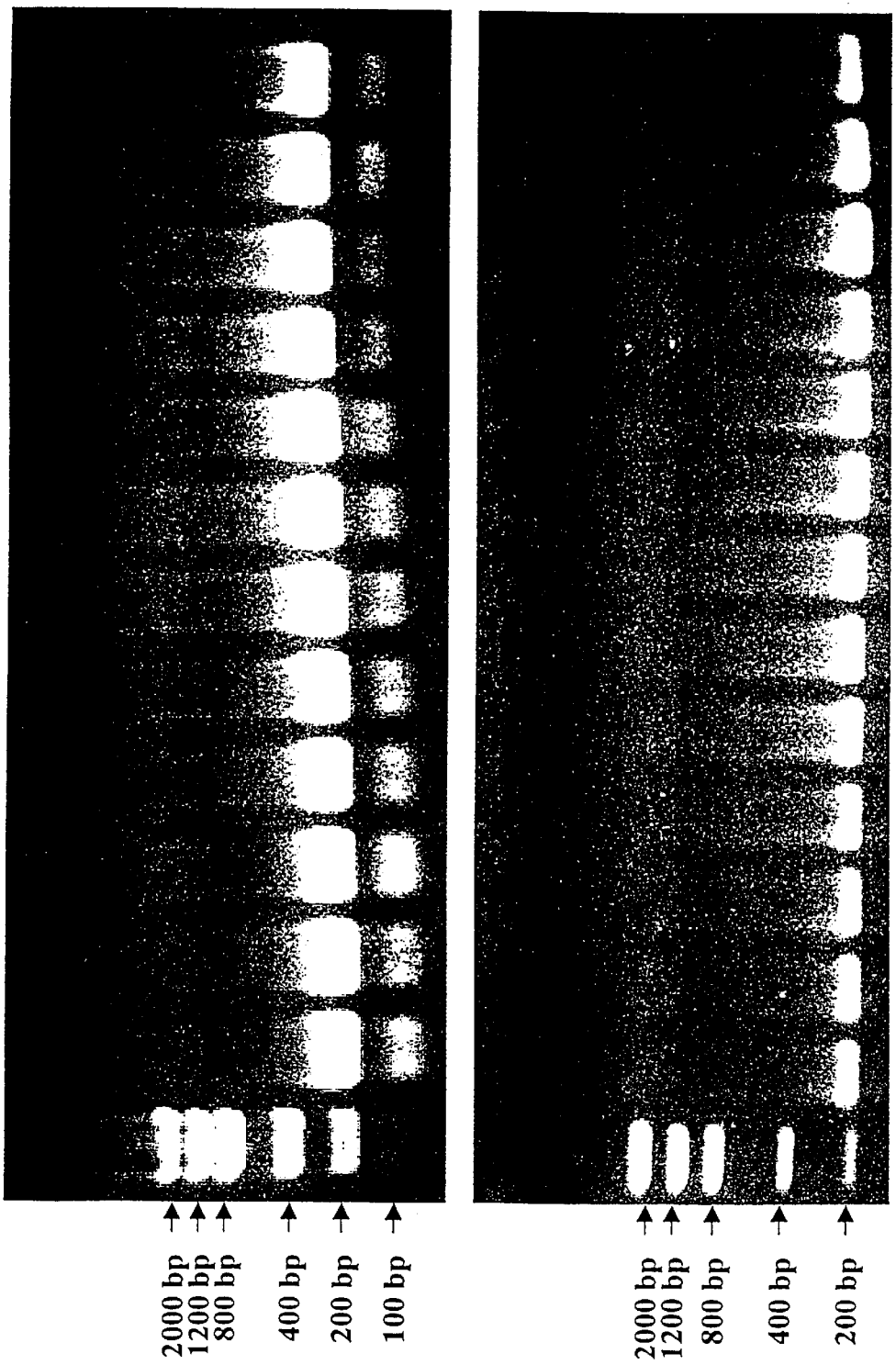
FIG. 3. PCR products of bloodstains on FTA paper processed with the precipitation method of the present disclosure were compared with PCR products of amplified genomic DNA generated from bloodstains on FTA paper using the precipitation method and the DNA amplification method of the present disclosure. Upper panel: Agarose gel electrophoresis of bovine PCR products generated directly from bloodstains on FTA paper that were processed with the precipitation method of the present disclosure. Lane 1, DNA molecular size marker; lanes 2–14, direct PCR products from the bloodstain samples of 13 individual animals. Lower panel: Agarose gel electrophoresis of bovine PCR products generated using genomic DNA amplified with the disclosed DNA amplification method using as DNA samples bloodstains on FTA paper that were processed with the disclosed precipitation method. Lane I, DNA molecular size marker; lanes 2–14, direct PCR products of DNA amplified from genomic DNA samples of 13 individual animals. It is apparent that DNA amplified by the method of the present disclosure can be used to accurately characterize DNA samples by PCR.

FIG. 3. shows the products of direct PCR of the known bovine SNP locus using DNA samples processed according to the disclosed precipitation method (upper panel), and the identical DNA samples processed according to the disclosed precipitation and DNA amplification method (lower panel). The PCR products are approximately 200 bp in length, which is the same as that calculated from the known DNA sequence. The visual image of the agarose gel indicates that the method for amplifying DNA of the present disclosure generates DNA that can be readily genotyped using PCR. Additionally, the DNA amplification method generates significantly greater amounts of genomic DNA than can be directly isolated from FTA paper. Increasing the amount of available genomic DNA by DNA amplification for genotyping will allow for more extensive analysis of an organism's genotype.

EXAMPLE 3

To compare the efficiency of the presently disclosed method of DNA amplification, DNA samples stored on FTA paper were first processed using the presently disclosed precipitation method or the commercial FTA Purification Reagent protocol, and then amplified according to the disclosed DNA amplification method. Two sets of punches from six different bloodstains stored on FTA paper were first treated using either the disclosed precipitation method or the FTA Purification Reagent protocol as outlined in Example 1. Next, the two sets of DNA samples were amplified according to the disclosed DNA amplification method, as outlined in Example 2.

Figure 4:
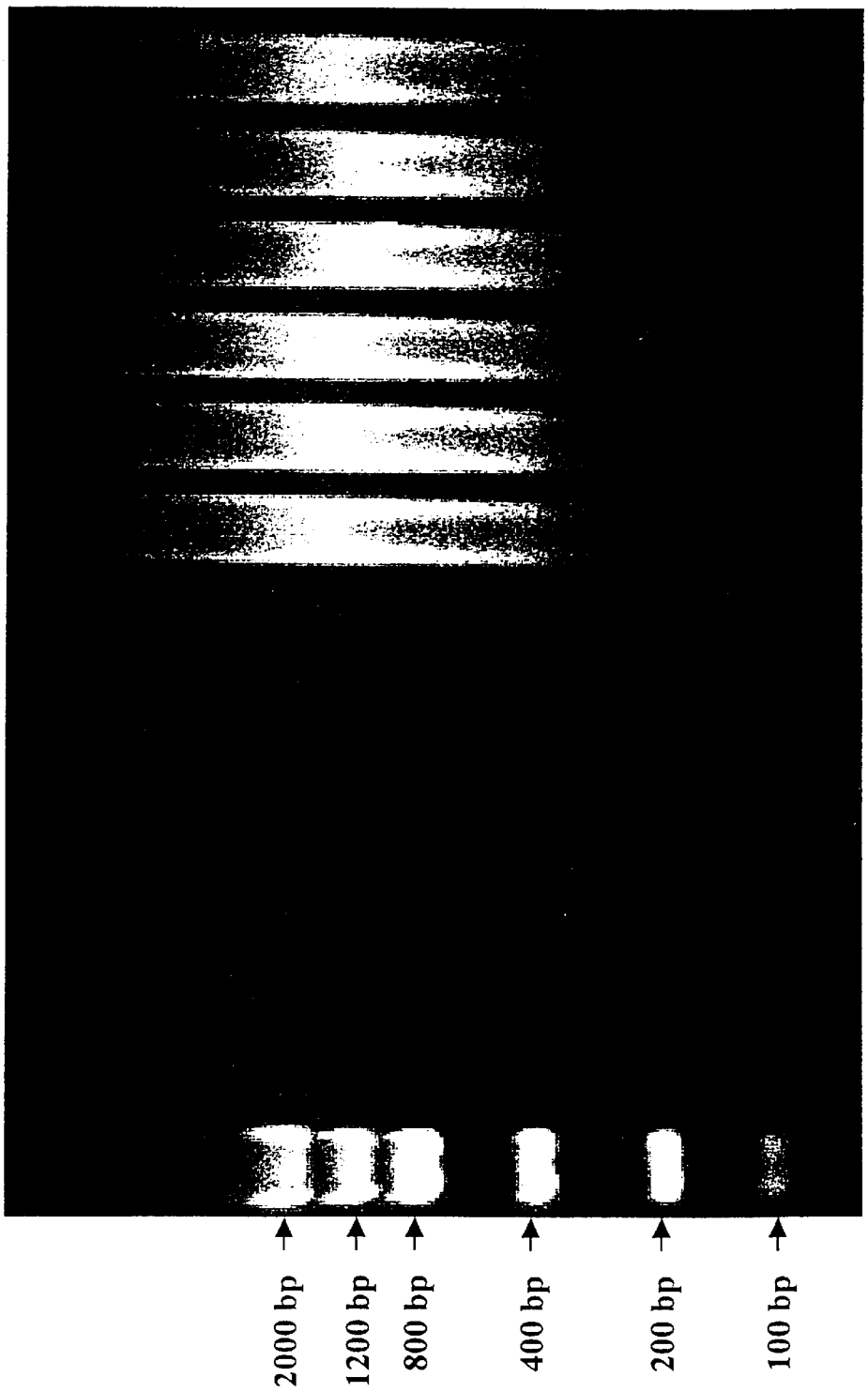
FIG. 4. Genomic DNA amplification from bloodstains on FTA paper, comparing the commercial FTA Purification Reagent system with the precipitation method of the present disclosure. Identical sets of DNA samples were first processed using the commercial FTA Purification Reagent system or the presently disclosed precipitation method, and then the DNA samples were amplified using the DNA amplification method of the present disclosure. Lane 1, DNA molecular size marker; lanes 2–7, genomic DNA amplification of 6 bloodstains on FTA paper processed using the commercial FTA Purification Reagent; lanes 8–13, genomic DNA amplification of 6 bloodstains on FTA paper processed using the precipitation method of the present disclosure. It is readily apparent that the disclosed method of DNA amplification yields far more amplified genomic DNA products when the disclosed precipitation method is used to process DNA samples on FTA paper than when the FTA Purification Reagent is used.

FIG. 4. demonstrates the results of genomic DNA amplification using the disclosed method of DNA amplification. The figure compares the efficiency of the disclosed DNA amplification method when the DNA sample is processed using the FTA Purification Reagent protocol (lanes 2–7) versus the disclosed precipitation method (lanes 8–13). FIG. 4. clearly demonstrates that the presently disclosed DNA amplification method generates much greater quantities of genomic DNA from bloodstains on FTA paper processed with the disclosed precipitation method than with the commercial FTA Purification Reagent system.

EXAMPLE 4

To demonstrate the general applicability of the presently disclosed method of DNA amplification to amplify DNA, a series of generic DNA sequences were used to generate first primers and second primers for amplifying genomic DNA. Each DNA sample on FTA paper was first processed using the presently disclosed precipitation method as outlined in Example 1. Next, the processed DNA samples were amplified according to the disclosed DNA amplification method, as outlined in Example 2, except that a different set of primers was used in each reaction. Each set of primers included a second primer as listed below, and a first primer with the same generic sequence as the second primer at its 5' end and 6 random nucleotides at its 3' end:

5'-ACAACGCAGAGTAAGCAGTGGTA-3', SEQ ID NO:3;

5'-ACAACGGTAGCAGAGTAAGCAGT-3', SEQ ID NO:4;

5'-GAGTAAGCAGTACAACGGTAGCA-3', SEQ ID NO:5;

5'-GAGGCATAAGCAGTACAACGGTA-3', SEQ ID NO:6;

5'-CAACGGTAGAGGCATAAGCAGTA-3', SEQ ID NO:7;

5'-GGCATAAGCAGTACAACGGTAGA-3', SEQ ID NO:8;

5'-AACGGTAGAGGCATAAGCAGTAC-3', SEQ ID NO:9;

5'-AGTACAACGGTAGAGGCATAAGC-3', SEQ ID NO:10;

5'-AAGCAGTACAACGGTAGAGGCAT-3', SEQ ID NO:11;

5'-CGGTAGAGGCATAAGCAGTACAA-3', SEQ ID NO:12.

For example, in the primer set that included the second primer having the sequence of SEQ ID NO:3, the first primer in the same DNA amplification reaction had the sequence 5'-ACAACGCAGAGTAAGCAGTGGTANNNNNN-3' (SEQ ID NO:17).

Figure 5:
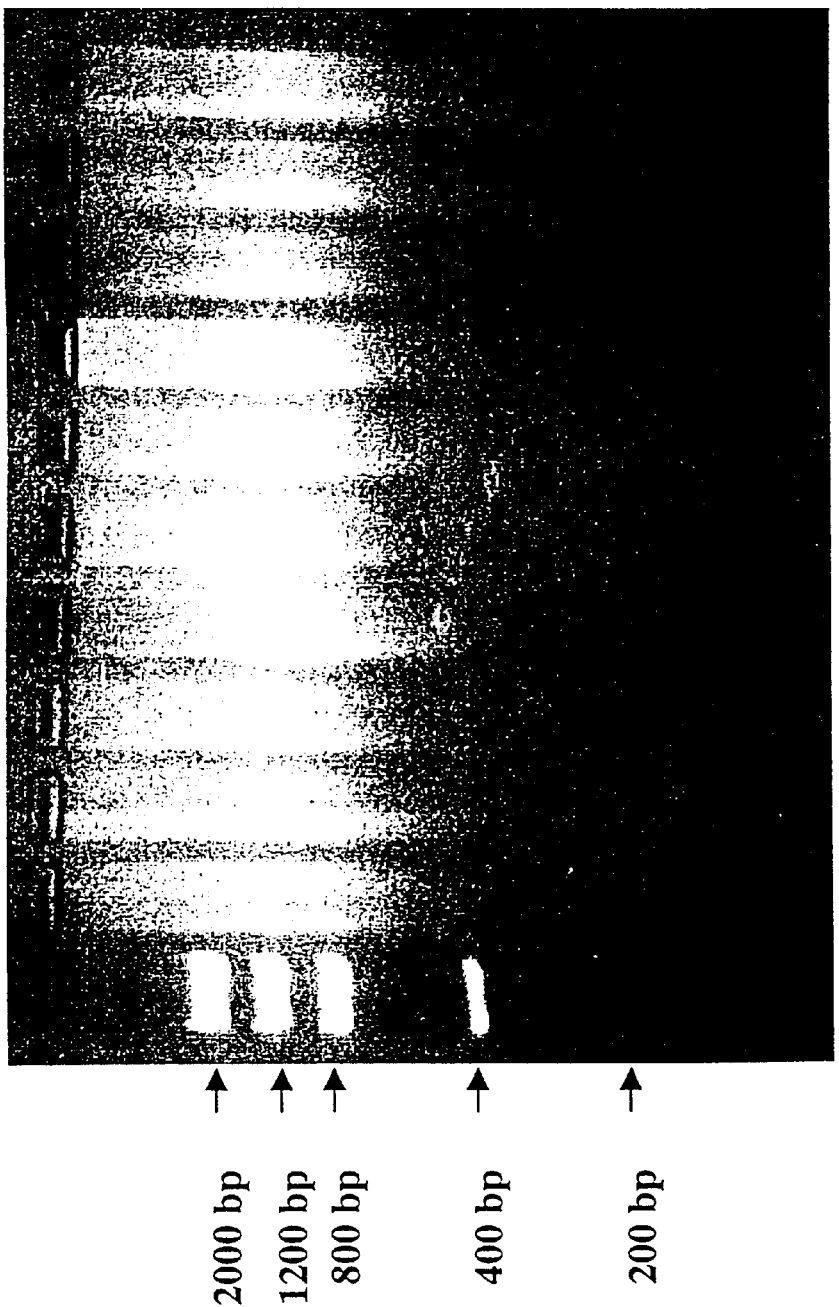
FIG. 5. Genomic DNA amplification of bloodstains stored on FTA paper using the presently disclosed DNA amplification method. The efficiency of a series of generic DNA sequences used to generate a first primer and a second primer for amplifying genomic DNA were compared. In each of the reaction mixtures for DNA amplification with the second primers listed below, the first primer used contained the same generic sequence as the second primer with 6 additional random nucleotides at the 3' end. Lane 1, DNA molecular size marker; lane 2, genomic DNA amplification with a second primer having the sequence of SEQ ID NO:3; lane 3, genomic DNA amplification with a second primer having the sequence of SEQ ID NO:4; lane 4, genomic DNA amplification with a second primer having the sequence of SEQ ID NO:5; lane 5, genomic DNA amplification with a second primer having the sequence of SEQ ID NO:6; lane 6, genomic DNA amplification with a second primer having the sequence of SEQ ID NO:7; lane 7, genomic DNA amplification with a second primer having the sequence of SEQ ID NO:8; lane 8, genomic DNA amplification with a second primer having the sequence of SEQ ID NO:9; lane 9, genomic DNA amplification with a second primer having the sequence of SEQ ID NO:10; lane 10, genomic DNA amplification with a second primer having the sequence of SEQ ID NO: 11; and lane 11, genomic DNA amplification with a second primer having the sequence of SEQ ID NO:12. The general ability of generic sequences designed according to the present disclosure to amplify DNA using the DNA amplification method is demonstrated by the uniform DNA amplification demonstrated in lanes 2–11.

As shown in FIG. 5., all of the primer sets were able to amplify genomic DNA from the samples stored on FTA paper. The primer sets used to amplify the genomic DNA in each lane of FIG. 5. used the following second primer: lane 2, SEQ ID NO:3; lane 3, SEQ ID NO:4; lane 4, SEQ ID NO:5; lane 5, SEQ ID NO:6; lane 6, SEQ ID NO:7; lane 7, SEQ ID NO:8; lane 8, SEQ ID NO:9; lane 9, SEQ ID NO:10; lane 10, SEQ ID NO: 11; and lane 11, SEQ ID NO: 12. FIG. 5. demonstrates that a person of skill in the art can design an enormous range of suitable generic sequences for first and second primers to amplify DNA according to the presently disclosed DNA amplification method in an efficient and uniform manner.

EXAMPLE 5

The reliability at the nucleotide sequence level of the disclosed method of DNA amplification was examined by analyzing PCR amplified products of a known bovine SNP locus using DNA amplified by the disclosed method and DNA directly from the FTA paper, similar to the comparison made in Example 2. In both experiments, the DNA samples stored on FTA paper were processed using the disclosed precipitation method as described in Example 1. Bloodstain samples were collected and stored on FTA paper for 8 individual bovine animals. The FTA paper samples were processed using the disclosed precipitation method, and genomic DNA was amplified from one set of samples using the disclosed method of DNA amplification as described in Example 2. The set of dehydrated DNA samples and amplified DNA samples were then subjected to PCR amplification as described in Example 2. The PCR products for each set were subsequently analyzed in a set of Doublecode OLA reactions, which were designed to detect SNP variations among the 8 different individual bovine animals.

Figure 6:
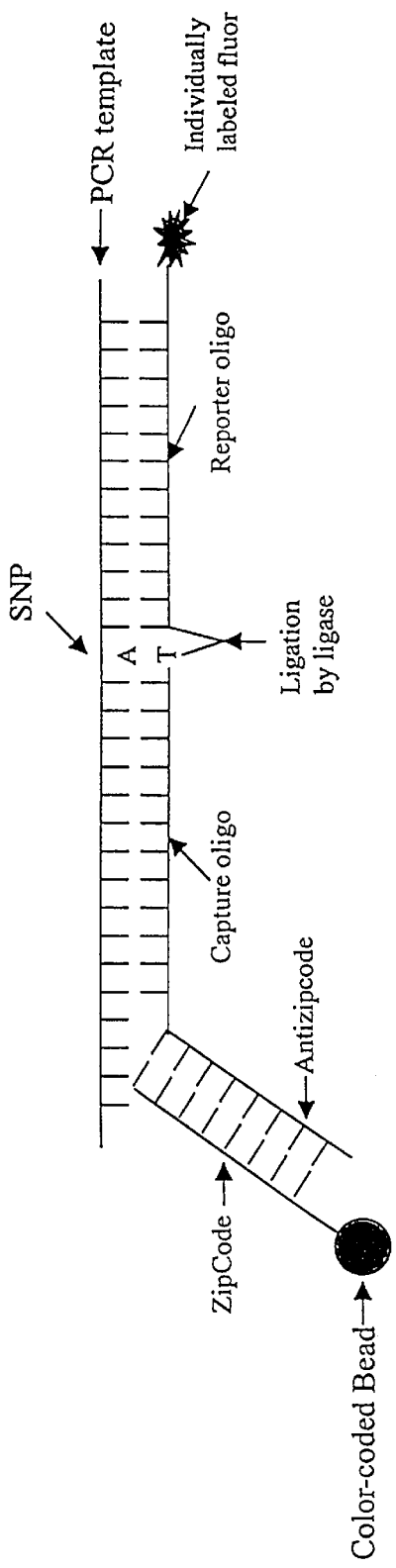
FIG. 6. Diagram to illustrate the Doublecode OLA (oligonucleotide ligation assay) reaction to detect SNP variations in a DNA sample. The upper diagram illustrates one option for performing OLA using a labeled Reporter oligonucleotide. The disadvantage of this technique is that a Reporter oligonucleotide specific to a single SNP must be individually labeled by a fluor. Since a new labeled Reporter oligonucleotide must be generated for each SNP genotyped, this method is an expensive option for large-scale genotyping. The lower diagram illustrates the Doublecode OLA reaction, which offers a significant improvement over the above method because it uses a labeled generic AntiSignalcode oligonucleotide that can be produced in large quantities and utilized for detecting any SNP. This AntiSignalcode oligonucleotide is used with a Reporter oligonucleotide that contains the reverse complement of the AntiSignalcode (Signalcode sequence), as well as a region complementary to a single SNP. Thus, this technique provides a less expensive option for detecting SNPs than the technique illustrated in the upper panel.
Figure 6:
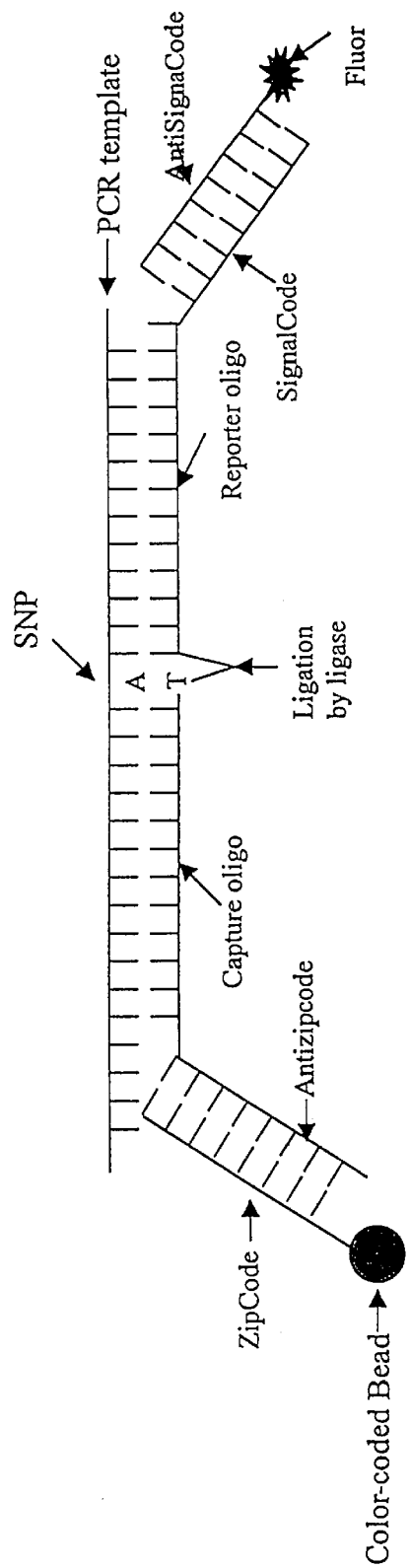

Doublecode OLA for SNP detection has been described in U.S. Application Ser. No. 09/755,628, abandoned, incorporated herein by reference, and is illustrated in FIG. 6. As illustrated in FIG. 6., Doublecode OLA requires four different oligonucleotides for SNP detection. A melting temperature (Tm) of around 55° C. was used for each of the four oligonucleotides utilized in the Doublecode OLA. The oligonucleotides used in the Doublecode OLA method, however, may be of any design that facilitates hybridization and the OLA reaction, and are not dependent on a particular Tm. The Tm of an oligonucleotide can be calculated and the length adjusted accordingly by one of skill in the art using a variety of computer software programs, such as Oligo Analyzer, which is available at the website www@idtdna.com. All of the oligonucleotides and their modifications utilized in Doublecode OLA reactions are commercially available.

The first oligonucleotide is an address specific Zipcode oligonucleotide. The sequence of the Zipcode oligonucleotide is derived from randomly selected nucleotides, and the 5' end of the Zipcode is substituted by an amino group with a $C_{12}$ spacer. A color-coded bead is attached to the 5' end of the Zipcode oligonucleotide via a coupling reaction catalyzed by 1-ethyl-3-(3-dimethylaminopropyl) carbodiimide hydrochloride (EDC). In one embodiment the color-coded bead is the Luminex color-coded bead. The Luminex color-coded beads have been specially modified with carboxyl groups on their surfaces. Carbodiimide catalyzes the formation of amide bonds between carboxylic acids and amines by activating carboxyl to form an O-urea derivative. This derivative reacts readily with nucleophiles, such as amine, to bind the Zipcode oligonucleotide to the surface of the bead.

The second oligonucleotide is a Capture oligonucleotide, which is composed of the complementary sequence on the 5' side of the target SNP plus one of the two SNP nucleotides at its 3' end. The Capture oligonucleotide is fitted with an AntiZipcode sequence at its 5' end which is the reverse complement of the Zipcode sequence selected above. The AntiZipcode sequence at the 5' end of the Capture oliogonucleotide will hybridize with the Zipcode oligonucleotide with a color-coded bead, while the 3' end of the Capture oligonucleotide will hybridize with a specific location in the target DNA.

The third oligonucleotide is the Reporter oligonucleotide, which is composed of the complementary sequence on the 3' side (downstream) of the target SNP. The Reporter oligonucleotide is fitted with another randomly selected sequence termed the Signalcode at its 3' end. The 5' end hydroxyl group of the Reporter oligonucleotide is substituted with a phosphate group, which facilitates a ligation reaction catalyzed by Taq ligase with the Capture oligonucleotide if the latter anneals perfectly at its 3' end with the SNP in the target DNA. The fourth oligonucleotide is the AntiSignalcode oligonucleotide, which is the reverse complement of the random Signalcode sequence selected above. The 3' end of the AntiSignalcode oligonucleotide is fitted with a biotin that can be subsequently stained by strepavidin-phycoerythrin conjugate.

Doublecode OLA to detect SNPs in the two sets of PCR amplification products of the 8 different individual bovine was performed in a reaction mixture containing the Zipcode oligonucleotide, Capture oligonucleotide, Reporter oligonucleotide, AntiSignalcode oligonucleotide, and Taq ligase. If the specific SNP designed to be detected by the oligonucleotides was present in the PCR products, the Capture oligonucleotide was ligated to the Reporter oligonucleotide by Taq ligase, and in a single hybridization reaction simultaneously sorted by the color-coded beads on the Zipcode oligonucleotide as well as stained by a fluor or biotin-labeled AntiSignalcode oligonucleotide. The fluorescence of the stained bead was measured on a flow cytometer.

The three ZipCode oligonucleotides used in the reactions were 5'-$NH_2$-CGACTCCCTGTTTGTGATGGACCAC-3' (SEQ ID NO:18); 5'-$NH_2$-CTTTTCCCGTCCGTCATCGCTCAAG-3' (SEQ ID NO:19); and 5'-$NH_2$-GGCTGGGTCTACAGATCCCCAACTT-3' (SEQ ID NO:20). The Zipcode oligonucleotides were coupled to beads according to the following procedure. The beads were dispersed in 100 µL of 0.1 M MES (pH 4.5). The amino-substituted oligonucleotides were added to a final concentration of 2 µM. Next, 5 µl of freshly made EDC solution (1-ethyl-3-[3-dimethylaminopropyl] carbodiimide hydrochloride, 100 µg/µl) was added to the reaction and incubated for 20 minutes at room temperature in the dark. Addition of the EDC solution and the 20 minute incubation was repeated. Afterwards, the beads were washed with 0.02% Tween 20 and then 0.1% SDS. The beads were then resuspended in TE buffer.

Three Capture oligonucleotides used in the reactions were 5'-gtggtccatcacaaacagggagtcgGAAGTCCCAGCTCTGACCTCTCCGG-3' (SEQ ID NO:21), 5'-cttgagcgatgacggacgggaaaagGAAGTCCCAGCTCTGACCTCTCCGT-3' (SEQ ID NO:22), and 5'-aagttggggatctgtagacccagccGAAGTCCCAGCTCTGACCTCTCCGM-3' (SEQ ID NO:23). The "M" in SEQ ID NO:23 is the degenerate nucleotide code for A or C. In the Capture oligonucleotides, the sequence in small letters is the AntiZipcode sequence and the sequence in capital letters is the target sequence 5' upstream of the SNP to be detected. The oligonucleotides having the sequence of SEQ ID NO:21 and SEQ ID NO:22 are identical except that the first has the nucleotide G at its 3' end and the second has the nucleotide T at its 3' end, which reflect the two alternate SNP nucleotides located at that position in the bovine genome. The sequence of the Reporter oligonucleotide used was In the Reporter oligonucleotide, the sequence in small letters is the Signalcode sequence and the sequence in capital letters is the target sequence 3' downstream of the target SNP.

The Doublecode OLA reactions were each carried out in a 20 µl reaction mixture containing: 1×Taq ligase buffer, 0.5 pmol of Capture oligonucleotide, 5.0 pmol of Reporter oligonucleotide with the 5' Signalcode region, and 20 ng of PCR products. The thermocycling program for the reaction mixtures was 96° C. for 2 minutes, followed by 55 cycles of 94° C. for 15 seconds and 37° C. for 1 minute.

After the thermocycling program was completed, the products were sorted and stained to genotype each of the 8 bovine individuals. The AntiSignalcode oligonucleotide used to sort the reaction products was 5'-ctgaacggtagcatcttgac-biotin-3' (SEQ ID NO:24). The sequence of the AntiSignalcode oligonucleotide is reverse complementary to the Signalcode sequence at the 5' end of the SignalCode Reporter oligonucleotide. The reaction products were simultaneously sorted by the color-coded beads on the Zipcode oligonucleotides and hybridized with the biotinylated AntiSignalcode oligonucleotides in a single hybridization. These reactions were each carried out in a 50 µl hybridization mixture containing: 1×TMAC buffer (2.5 M TMAC (tetramethyl ammonium chloride), 0.15% SDS, 3 mM EDTA, and 75 mM Tris-HCl (pH 8.0)), 5000 Zipcode oligonucleotides with the color-coded beads for each SNP, 2.5 pmol of biotinylated AntiSignalcode oligonucleotides, and 20 µl of the Doublecode OLA reaction mixture. The hybridization reaction mixtures were incubated at 95° C. for 5 minutes and then at 50° C. for 15 minutes.

The hybridized biotinylated AntiSignalcode oligonucleotides were stained with fluorescent strepavidin-phycoerythrin conjugate in a reaction that contained 1×TE buffer and the conjugate (10 µg/ml). The reaction was incubated at room temperature for 5 minutes, and the fluorescent signal of the color-coded beads was measured in a Lumninex 100 flow cytometer. Table 4 summarizes the genotyping results of DNA samples processed according to the disclosed precipitation and DNA amplification methods for 8 individual bovine animals. Table 5 summarizes the genotyping results of DNA samples processed according to the disclosed precipitation method only for the same 8 bovine animals. As shown below, both methods give the identical genotype results for each bovine animal:

TABLE 4

[00221]

|  | 1 | 2 | 3 | 4 | 5 | 6 | 7 | 8 |
|---|---|---|---|---|---|---|---|---|
| G Bead | 26 | 147 | 99 | 31 | 118 | 106 | 113 | 112 |
| T Bead | 119 | 87 | 106 | 132 | 86 | 188 | 93 | 78 |
| A/C Bead | 33 | 40 | 35 | 35 | 26 | 47 | 36 | 23 |
| Genotype | T | G/T | G/T | T | G/T | G/T | G/T | G/T |

*relative fluorescent intensity

TABLE 5

[00222]

|  | 1 | 2 | 3 | 4 | 5 | 6 | 7 | 8 |
|---|---|---|---|---|---|---|---|---|
| G Bead | 21 | 140 | 140 | 20 | 137 | 139 | 152 | 132 |
| T Bead | 176 | 120 | 113 | 138 | 122 | 114 | 103 | 113 |
| A/C Bead | 35 | 39 | 36 | 42 | 40 | 32 | 41 | 38 |
| Genotype | T | G/T | G/T | T | G/T | G/T | G/T | G/T |

*relative fluorescent intensity

The above results demonstrate that the disclosed method of DNA amplification is able to reliably amplify genomic DNA with high fidelity, which indicates that this method can be used to accurately genotype multiple loci within a single organism, even if only a very limited amount of DNA is available.

EXAMPLE 6

To further investigate the fidelity of the presently disclosed DNA amplification method, genomic DNA was isolated from the sperm of 8 individual bovine animals. The genomic DNA isolated from the sperm was subjected to PCR amplification using the protocol described in Example 2, except that two different primers were used to amplify the DNA: 5'-CCAGATTCTTTCGGCAGGTA-3' (SEQ ID NO:25), and 5'-CATGGGAACCAGGCTGAAT (SEQ ID NO:26). The PCR products were sequenced using the dideoxynucleotide chain termination method described by Sanger et al. (*Proc Natl Acad Sci USA* 74:5463–67, 1977). The genotype for each of the 8 bovine individual animals is listed below in Table 6.

TABLE 6

|  | 1 | 2 | 3 | 4 | 5 | 6 | 7 | 8 |
|---|---|---|---|---|---|---|---|---|
| Genotype | T | T | G | T | T | T | G | G/T |

Next, genomic DNA isolated from sperm of the same 8 individual bovine animals was subjected to DNA amplification using the disclosed DNA amplification method as described in Example 2. Twenty nanograms of starting genomic DNA was amplified. The amplified DNA samples were then subjected to PCR amplification as described above, and finally the PCR products were analyzed in a set of Doublecode OLA reactions, as described in Example 5, which were designed to detect SNP variations among the 8 different individual bovine animals. Table 7 summarizes the genotyping results of the sperm DNA amplified according to the DNA amplification methods of the present disclosure.

TABLE 7

[00227]

|  | 1 | 2 | 3 | 4 | 5 | 6 | 7 | 8 |
|---|---|---|---|---|---|---|---|---|
| G Bead | 24 | 22 | 227 | 18 | 31 | 21 | 277 | 88 |
| T Bead | 133 | 120 | 35 | 178 | 174 | 93 | 28 | 102 |
| A/C Bead | 31 | 27 | 41 | 37 | 37 | 31 | 24 | 41 |
| Genotype | T | T | G | T | T | T | G | G/T |

*relative fluorescent intensity

A comparison of the results in Tables 6 and 7 demonstrates that DNA products are reliably and consistently amplified from genomic DNA using the disclosed DNA amplification method. Direct sequencing of PCR products generated from genomic DNA yield the exact same genotype results as Doublecode OLA analysis of PCR products generated from DNA amplified using the DNA amplification method of the present disclosure. These results demonstrate once again that the disclosed method of DNA amplification is able to reliably amplify genomic DNA with high fidelity.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the methods described herein without departing from the concept, spirit and scope of the invention. More specifically, it will be apparent that certain agents that are chemically or physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A method of amplifying DNA, the method comprising:
   (a) providing a single reaction mixture comprising:
      (i) a DNA sample;
      (ii) a first primer comprising a random sequence of nucleotides at its 3' end and a generic sequence 5' of the random nucleotides;
      (iii) a second primer comprising the generic sequence of the first primer and lacking the random sequence of the first primer; and
      (iv) a heat-stable DNA polymerase;
   (b) subjecting the DNA sample to DNA amplification wherein the first primer anneals to the DNA to allow the heat-stable DNA polymerase to produce a DNA product; and
   (c) subjecting the DNA product of step (b) to DNA amplification wherein the second primer anneals to the DNA product.

2. The method of claim 1, wherein the heat-stable DNA polymerase is Taq DNA polymerase.

3. The method of claim 1, wherein the DNA amplification of step (b) comprises the steps of denaturing the DNA product; annealing the first primer with the DNA to allow the formation of a DNA-primer hybrid; and incubating the DNA-primer hybrid to allow the heat-stable DNA polymerase to synthesize a DNA product.

4. The method of claim 3, wherein the DNA amplification steps are repeated at least one time.

5. The method of claim 1, wherein the DNA amplification of step (c) comprises the steps of denaturing the DNA product; annealing the second primer with the DNA product to allow the formation of a DNA-primer hybrid; and incubating the DNA-primer hybrid to allow the heat-stable DNA polymerase to synthesize a second DNA product.

6. The method of claim 5, wherein the annealing temperature is higher than the optimal annealing temperature of the random sequence of nucleotides of the first primer.

7. A method of identifying a polymorphism, the method comprising:
   (a) providing a single reaction mixture comprising:
      (i) a DNA sample;
      (ii) a first primer comprising a random sequence of nucleotides at its 3' end and a generic sequence 5' of the random nucleotides;
      (iii) a second primer comprising the generic sequence of the first primer and lacking the random sequence of the first primer; and
      (iv) a heat-stable DNA polymerase;
   (b) subjecting the DNA sample to DNA amplification wherein the first primer anneals to the DNA to allow the heat-stable DNA polymerase to produce a DNA product;
   (c) subjecting the DNA product of step (b) to DNA amplification wherein the second primer anneals to the DNA product to allow the heat-stable DNA polymerase to produce amplified DNA products; and
   (d) analyzing the amplified DNA products of step (c) to identify a polymorphism.

8. The method of claim 7, wherein the polymorphism is a single nucleotide polymorphism (SNP).

9. The method of claim 8, wherein the SNP is identified by Oligonucleotide Ligation Assay (OLA), Doublecode OLA, sequencing, Single Base Extension Assay, allele specific primer extension, or mismatch hybridization.

10. A method of amplifying DNA, the method comprising:
    (a) providing a single reaction mixture comprising:
       (i) a DNA sample to be amplified;
       (ii) a first primer comprising a random sequence of nucleotides at its 3' end and a generic sequence 5' of the random sequence;
       (iii) a second primer comprising the generic sequence and lacking the random sequence of the first primer; and
       (iv) a heat-stable DNA polymerase;
    (b) heating the single reaction mixture to a temperature that denatures the DNA to be amplified;
    (c) cooling the single reaction mixture to a temperature that allows the random sequence of the first primer to hybridize to its complement DNA and incubating the reaction mixture to allow synthesis of a DNA product by the heat-stable DNA polymerase;
    (d) repeating steps (b) and (c) at least one time.

11. A method of identifying a polymorphism, the method comprising:
    (a) precipitating a DNA sample on a solid medium;
    (b) providing a single reaction mixture comprising:
       (i) the DNA sample;
       (ii) a first primer comprising a random sequence of nucleotides at its 3' end and a generic sequence 5' of the random nucleotides;
       (iii) a second primer comprising the generic sequence of the first primer and lacking the random sequence of the first primer; and
       (iv) a heat-stable DNA polymerase;
    (c) subjecting the DNA sample to DNA amplification by the heat-stable DNA polymerase wherein the first primer anneals to the DNA to allow the heat-stable DNA polymerase to produce a DNA product;
    (d) subjecting the DNA product of step (c) to DNA amplification by the heat-stable DNA polymerase wherein the second primer anneals to the DNA product to allow the heat-stable DNA polymerase to produce a second DNA product; and
    (e) analyzing the second DNA product to identify a polymorphism.

12. The method of claim 11, wherein the DNA sample is precipitated with salt and alcohol, and rinsed with alcohol.

13. A method of amplifying DNA, the method comprising:
    (a) providing a single reaction mixture comprising:
       (i) a DNA sample;
       (ii) a first primer comprising a random sequence of nucleotides at its 3' end and a generic sequence 5' of the random nucleotides; and
       (iii) a second primer comprising the generic sequence of the first primer and lacking the random sequence of the first primer;
    (b) subjecting the DNA sample to DNA amplification by a heat-stable DNA polymerase wherein the first primer anneals to the DNA to produce a DNA product.

14. The method of claim 13, further comprising subjecting the DNA product of step (b) to DNA amplification by a heat-stable DNA polymerase wherein the second primer anneals to the DNA product.

15. The method of claim 13, wherein the DNA amplification of step (b) comprises the steps of denaturing the DNA product; annealing the first primer with the DNA to allow the formation of a DNA-primer hybrid; and incubating the DNA-primer hybrid to allow the heat-stable DNA polymerase to synthesize a DNA product.

16. The method of claim 15, wherein the DNA amplification steps are repeated at least one time.

17. The method of claim 14, wherein the DNA amplification comprises the steps of denaturing the DNA product; annealing the second primer with the DNA product to allow the formation of a DNA-primer hybrid; and incubating the DNA-primer hybrid to allow the heat-stable DNA polymerase to synthesize a second DNA product.

18. The method of claim 17, wherein the second DNA product is flanked by the generic sequence and the reverse complement of the generic sequence.

19. The method of claim 17, wherein the annealing temperature is higher than the optimal annealing temperature of the random sequence of nucleotides of the first primer.

20. The method of claim 17, wherein the DNA amplification steps are repeated about 30 to about 40 times.

21. The method of claim 13, wherein the heat-stable DNA polymerase is Taq DNA polymerase.

22. The method of claim 13, wherein the first primer comprises about 4 to about 8 random nucleotides at its 3' end.

23. The method of claim 13, wherein the generic sequence of the first primer is about 15 to about 28 nucleotides in length.

24. The method of claim 13, wherein the random nucleotides of the first primer are G:C rich.

25. The method of claim 13, wherein the random nucleotides of the first primer are A:T rich.

26. The method of claim 13, wherein the generic sequence of the first primer comprises a single or multiple restriction enzyme recognition site.

27. The method of claim 13, wherein the DNA sample is selected from the group consisting of genomic DNA, microdissected chromosome DNA, yeast artificial chromosome (YAC) DNA, cosmid DNA, phage DNA, P1 derived artificial chromosome (PAC) DNA, and bacterial artificial chromosome (BAC) DNA.

28. The method of claim 13, wherein the DNA sample is selected from the group consisting of mammalian DNA, plant DNA, yeast DNA, viral DNA, and prokaryotic DNA.

29. The method of claim 13, wherein the DNA sample is obtained from a human, bovine, porcine, ovine, equine, rodent, avian, fish, shrimp, plant, yeast, virus, or bacteria.

30. The method of claim 13, wherein the DNA sample is tissue on a solid medium.

31. The method of claim 13, wherein the DNA sample is obtained from a buccal swab, a nose swab, blood, cord blood, amniotic fluid, embryonic tissue, hair, endothelial cells, hoof clippings, or fingernail clipping.

32. The method of claim 13, further comprising genotype analysis of the amplified DNA product.

33. The method of claim 13, further comprising identifying a single nucleotide polymorphism (SNP) in the amplified DNA product.

34. The method of claim 33, wherein the SNP is identified by Oligonucleotide Ligation Assay (OLA), Doublecode OLA, sequencing, Single Base Extension Assay, allele specific primer extension, or mismatch hybridization.

* * * * *

SEQUENCE LISTING

<160> NUMBER OF SEQ ID NOS: 26

<210> SEQ ID NO 1
<211> LENGTH: 28

```
<212> TYPE: DNA
<213> ORGANISM: Artificial Sequence
<220> FEATURE:
<221> NAME/KEY: modified_base
<222> LOCATION: (24)..(28)
<223> OTHER INFORMATION: N = A, G C or T
<223> OTHER INFORMATION: Description of Artificial Sequence: Synthetic
      Primer

<400> SEQUENCE: 1
tagcagtggt aacaacgcag agannnnn                                          28

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 2
tagcagtggt aacaacgcag aga                                               23

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 3
acaacgcaga gtaagcagtg gta                                               23

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 4
acaacggtag cagagtaagc agt                                               23

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 5
gagtaagcag tacaacggta gca                                               23

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 6
gaggcataag cagtacaacg gta                                               23
```

```
<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 7
caacggtaga ggcataagca gta                                              23

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 8
ggcataagca gtacaacggt aga                                              23

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 9
aacggtagag gcataagcag tac                                              23

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 10
agtacaacgg tagaggcata agc                                              23

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 11
aagcagtaca acggtagagg cat                                              23

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 12
cggtagaggc ataagcagta caa                                              23

<210> SEQ ID NO 13
```

```
<211> LENGTH: 23
<212> TYPE: DNA
<213> ORGANISM: Bovine

<400> SEQUENCE: 13
cctttccctc tagcatcaag tta                                            23

<210> SEQ ID NO 14
<211> LENGTH: 21
<212> TYPE: DNA
<213> ORGANISM: Bovine

<400> SEQUENCE: 14
cagactgtgt gcttcctaca g                                              21

<210> SEQ ID NO 15
<211> LENGTH: 21
<212> TYPE: DNA
<213> ORGANISM: Bovine

<400> SEQUENCE: 15
ccagcagttc tgaatgaaag t                                              21

<210> SEQ ID NO 16
<211> LENGTH: 18
<212> TYPE: DNA
<213> ORGANISM: Bovine

<400> SEQUENCE: 16
acacacagag gccgtgta                                                  18

<210> SEQ ID NO 17
<211> LENGTH: 29
<212> TYPE: DNA
<213> ORGANISM: Artificial Sequence
<220> FEATURE:
<223> OTHER INFORMATION: Description of Artificial Sequence:  Synthetic
      Primer
<221> NAME/KEY: modified_base
<222> LOCATION: (24)..(29)
<223> OTHER INFORMATION: N = A, G, C or T

<400> SEQUENCE: 17
acaacgcaga gtaagcagtg gtannnnnn                                      29

<210> SEQ ID NO 18
<211> LENGTH: 25
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 18
cgactccctg tttgtgatgg accac                                          25

<210> SEQ ID NO 19
<211> LENGTH: 25
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 19
cttttcccgt ccgtcatcgc tcaag                                          25
```

<210> SEQ ID NO 20
<211> LENGTH: 25
<212> TYPE: DNA
<213> ORGANISM: Artificial Sequence
<220> FEATURE:
<223> OTHER INFORMATION: Description of Artificial Sequence: Synthetic Primer

<400> SEQUENCE: 20
ggctgggtct acagatcccc aactt                                              25

<210> SEQ ID NO 21
<211> LENGTH: 49
<212> TYPE: DNA
<213> ORGANISM: Bovine

<400> SEQUENCE: 21
tggtccatca caaacaggga gtcggaagtc ccagctctga cctctccgg                    49

<210> SEQ ID NO 22
<211> LENGTH: 50
<212> TYPE: DNA
<213> ORGANISM: Bovine

<400> SEQUENCE: 22
cttgagcgat gacggacggg aaaaggaagt cccagctctg acctctccgt                   50

<210> SEQ ID NO 23
<211> LENGTH: 49
<212> TYPE: DNA
<213> ORGANISM: Bovine

<400> SEQUENCE: 23
aagttgggga tctgtagacc cagccgaagt cccagctctg acctctccg                    49

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic Primer

<400> SEQUENCE: 24
ctgaacggta gcatcttgac                                                    20

<210> SEQ ID NO 25
<211> LENGTH: 20
<212> TYPE: DNA
<213> ORGANISM: Bovine

<400> SEQUENCE: 25
ccagattctt tcggcaggta                                                    20

<210> SEQ ID NO 26
<211> LENGTH: 19
<212> TYPE: DNA
<213> ORGANISM: Bovine

<400> SEQUENCE: 26
catgggaacc aggctgaat                                                     19